(12) United States Patent
Kunz et al.

(10) Patent No.: US 10,290,819 B2
(45) Date of Patent: May 14, 2019

(54) METAL COMPLEXES

(75) Inventors: Doris Kunz, Tuebingen (DE); Verena Gierz, Mannheim (DE)

(73) Assignee: Merck Patent GmbH (DE)

(*) Notice: Subject to any disclaimer, the term of this patent is extended or adjusted under 35 U.S.C. 154(b) by 1382 days.

(21) Appl. No.: 13/994,506

(22) PCT Filed: Dec. 13, 2011

(86) PCT No.: PCT/EP2011/006281
§ 371 (c)(1),
(2), (4) Date: Jun. 14, 2013

(87) PCT Pub. No.: WO2012/079741
PCT Pub. Date: Jun. 21, 2012

(65) Prior Publication Data
US 2013/0284977 A1 Oct. 31, 2013

(30) Foreign Application Priority Data

Dec. 15, 2010 (DE) .......... 10 2010 054 524
Jul. 4, 2011 (DE) .......... 10 2011 106 849

(51) Int. Cl.
| | | |
|---|---|---|
| H01L 51/00 | (2006.01) |
| C07F 1/00 | (2006.01) |
| C07F 11/00 | (2006.01) |
| C07F 13/00 | (2006.01) |
| C07F 15/00 | (2006.01) |
| H01L 51/50 | (2006.01) |

(52) U.S. Cl.
CPC .............. *H01L 51/009* (2013.01); *C07F 1/00* (2013.01); *C07F 11/00* (2013.01); *C07F 13/00* (2013.01); *C07F 15/002* (2013.01); *C07F 15/0033* (2013.01); *C07F 15/0086* (2013.01); *H01L 51/0084* (2013.01); *H01L 51/0085* (2013.01); *H01L 51/0087* (2013.01); *H01L 51/0088* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| 6,667,269 | B2 | 12/2003 | Olivier-Bourbigou et al. |
| 7,112,638 | B2 | 9/2006 | Nifant'ev et al. |
| 2009/0326237 | A1 | 12/2009 | Strassner et al. |
| 2011/0284799 | A1 | 11/2011 | Stoessel et al. |
| 2014/0152637 | A1 | 6/2014 | Fujita et al. |

FOREIGN PATENT DOCUMENTS

| JP | 63-127727 A | 5/1988 |
| JP | 63-192774 A | 8/1988 |
| JP | 2001-310132 A | 11/2001 |
| JP | 2003-519156 A | 6/2003 |
| JP | 2003-221579 A | 8/2003 |
| JP | 2003-245557 A | 9/2003 |
| JP | 2009-542026 A | 11/2009 |
| JP | 2014-141415 A | 8/2014 |
| WO | WO-2005/113704 A2 | 12/2005 |
| WO | WO-2008/000726 A1 | 1/2008 |
| WO | WO-2009/152133 A1 | 12/2009 |
| WO | WO-2010/086089 A1 | 8/2010 |

OTHER PUBLICATIONS

English translation of Aouial et al., "Syntheses de Bitriazoles-3(-5),1' Methyles en Position 1 ou 4 et de Bitriazoles-4,4", *J. Heterocyclic Chem.*, vol. 14, pp. 397-400 (1977).
Aouial et al., "Syntheses de Bitriazoles-3(-5),1' Methyles en Position 1 ou 4 et de Bitriazoles-4,4", *J. Heterocyclic Chem.*, vol. 14, pp. 397-400 (1977).
Tanaka et al., "Non-Photochemical Route to Chiral Disubstituted [7]Thiaheterohelicenes via Biaryl- and Carbonyl-Coupling Reactions", *J. Org. Chem.*, vol. 62, pp. 4465-4470 (1997).
Jalal et al., "Ab Initio and Density Functional Theory Studies of Perl-and Regioselectivity in 1,3-dipolar cycloaddition Reaction of 1,2-diazepine with Nitrile Oxide", *Journal of Molecular Structure: Theochem*, vol. 580, pp. 183-192 (2002).
Poyatos et al., "A planar chelating bitriazole N-heterocyclic carbene ligand and its rhodium(III) and dirhodium(II) complexes", *Chemical Communications* (Cambridge, United Kingdom), vol. 22, pp. 2267-2269 (2007).
Poyatos et al., "A Weak Donor, Planar Chelating Bitriazole N-Heterocyclic Carbene Ligand for Ruthenium(II), Palladium(II), and Rhodium", *Organometallic*, vol. 27, pp. 2128-2136 (2008).
Heckenroth et al., "On the Electronic Impact of Abnormal C4-Bonding in N-Heterocyclic Carbene Complexes", *Chem. Eur. Journal*, vol. 15, pp. 9375-9386 (2009).
Sanz et al., '($\eta^5$-arene)Ru(bis-NHC)' complexes for the reduction of CO2 to formate with hydrogen and by transfer hydrogenation with iPrOH, *Dalton Trans.*, vol. 39, pp. 6339-6343 (2010).
Gazzola et al., "Alkyne hydroarylation with palladium(II) complexes bearing chelating N-heterocyclic ligands: effect of non-coordinated nitrogens on catalyst efficiency", *New J. Chem.*, vol. 34, pp. 482-486 (2010).
International Search Report for PCT/EP2011/006281 dated Feb. 2, 2012.

*Primary Examiner* — Jay Yang
(74) *Attorney, Agent, or Firm* — Drinker Biddle & Reath LLP

(57) ABSTRACT

The present invention relates to bisimidazolium salts, to novel mono- and biscarbenes derived therefrom, and to metal complexes which contain corresponding mono- and biscarbenes as ligands, to a process for the preparation of the bisimidazolium salts according to the invention, the mono- and biscarbenes according to the invention and to the metal complexes according to the invention, and to the use of the bisimidazolium salts according to the invention, the mono- and biscarbenes according to the invention and to the use of the metal complexes according to the invention.

18 Claims, No Drawings

METAL COMPLEXES

RELATED APPLICATIONS

This application is a national stage application (under 35 U.S.C. § 371) of PCT/EP2011/006281, filed Dec. 13, 2011, which claims benefit of German Patent Application No. 10 2010 054 524.4, filed Dec. 15, 2010, and German Patent Application No. 10 2011 106 849.3, filed Jul. 4, 2011.

The present invention relates to bisimidazolium salts, to novel mono- and biscarbenes derived therefrom, and to metal complexes which contain corresponding mono- and biscarbenes as ligands, to a process for the preparation of the bisimidazolium salts according to the invention, the mono- and biscarbenes according to the invention and the metal complexes according to the invention, and to the use of the bisimidazolium salts according to the invention, the mono- and biscarbenes according to the invention and to the use of the metal complexes according to the invention.

Imidazolium and bisimidazolium salts and the preparation thereof are known from the literature. These are compounds which serve as precursor of N-heterocyclic carbenes and metal complexes thereof. The carbenes themselves can be used as nucleophilic organocatalysts. Metal complexes of N-heterocyclic carbenes can be used as metal catalysts (Herrmann, Angew. Chem. Int. Ed. 2002, 41, 1290-1309). These metal complexes can furthermore be used in electronic devices, for example as emitters in organic electroluminescent devices.

An important class of compounds in the area of N-heterocyclic carbenes are so-called biscarbenes, which contain two carbene units connected to one another. They can function as bidentate chelate ligands and thus help the corresponding metal complexes to achieve high stability. In particular, the bisimidazolium salts or biscarbenes which are bridged via one or more $CH_2$ units are known from the literature (Peris et al., Chem. Rev. 2009, 109, 3677-3707).

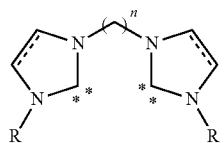

One feature of most biscarbene ligands is the possibility of also forming bimetallic complexes with rotation of the ligand structure.

Amongst the biscarbenes, there are only very few examples in which a direct N—N link of the two carbene units is present.

A very early example of N—N-linked biscarbenes comes from 1925 by Tschugajeff et al. (Z. Anorg. Allg. Chem. 1925, 37-42). However, the authors were unaware at this time that the compound isolated by them was a biscarbene complex. The carbene structure was first postulated in 1970 by Burke et al. (J. Am. Chem. Soc. 1970, 2555-2557) and by Shaw (Chem. Comm. 1970, 183), where Burke was able to provide structural evidence with an X-ray structural analysis. The structure of the Tschugajeff carbene is depicted below.

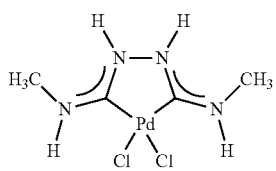

Various Tschugajeff carbenes have successfully been employed by Slaughter et al. as catalysts in the Suzuki-Miyaura reaction (Slaughter et al., Tetrahedron Lett. 2005, 46, 1399-1403 and Organometallics, 2006, 25, 491-505).

R. H. Crabtree et al. (Chem. Comm. 2007, 2267-2269 and Organometallics 2008, 27, 2128-2136) describe a triazole-based N—N-linked bisimidazolium salt and some of its metal complexes. However, it should be noted here that planar coordination does not automatically take place. Likewise, a non-chelating coordination to two metal centres with rotation of the ligand structure is observed.

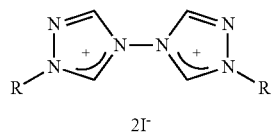

Peris et al. (Dalton Trans. 2010, 39, 6339-6343) describe the use of the ligand developed by Crabtree et al. for the preparation of ruthenium complexes for catalytic transfer hydrogenation.

A disadvantage of the system described by Crabtree et al. is that deprotonation of the bisimidazolium salt to give the biscarbene is not possible, since the molecule rearranges under the strongly basic reaction conditions and can no longer coordinate to metal centres. The synthesis of metal complexes starting from the free biscarbene is thus not possible, which restricts the choice of metal precursors. In addition, lower stability of the metal complexes is to be expected, since, in the case of ligand dissociation, decomposition of the free carbene would be expected.

The object of the present invention was therefore to develop a class of N—N-linked bisimidazolium salts which can serve as precursor for mono- and biscarbenes and metal complexes thereof. The rearrangement observed by Crabtree et al. is to be prevented, and furthermore the rotation about the N—N bond hindered in this way is to give preference to a chelating coordination in metal complexes. Furthermore, the invention was based on the object of providing processes for the preparation of the bisimidazolium salts, the mono- and biscarbenes and metal complexes thereof. Still a further object of the present invention was the provision of metal complexes which are suitable for use in catalysis and/or in electronic devices, in particular as emitters in organic electroluminescent devices.

This object is achieved by the provision of the metal complexes of the formulae (1), (2) and (3) described below and the provision of the ligands of the formulae (4) and (5) on which these metal complexes are based.

The metal complexes according to the invention are distinguished by high stability, which is possibly due to the fact that the biscarbene ligands have a rigid conformation with a suitable bite angle and can behave analogously to phenanthroline and bipyridine ligands.

The present application therefore relates to metal complexes of the following general formulae (1), (2) and (3),

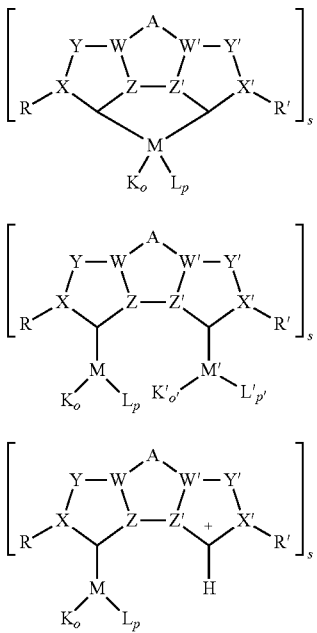

formula (1)

formula (2)

formula (3)

where the symbols and indices used have the following meanings:

M, M' is on each occurrence, identically or differently, a charged or uncharged metal atom selected from groups 1 to 13 of the Periodic Table of the Elements, the lanthanoids or the actinoids;

R, R' is, identically or differently independently of one another, hydrogen, straight-chain or branched alkyl having 1-20 C atoms, straight-chain or branched alkenyl having 2-20 C atoms and at least one double bond, straight-chain or branched alkynyl having 2-20 C atoms and at least one triple bond, saturated, partially or fully unsaturated cycloalkyl having 3-10 C atoms, which may be substituted by alkyl groups having 1-10 C atoms, unsubstituted or substituted aryl or aromatic ring system, unsubstituted or substituted heterocycle or heteroaromatic ring system or substituted or unsubstituted aralkyl or heteroaralkyl, where one or both substituents R and R' may be partially substituted in any desired position or fully substituted by halogen or partially substituted in any desired position by CN or $NO_2$, and halogen is selected from F, Cl, Br and I, and where a carbon atom of one or both substituents R and R' may be replaced by atoms and/or atom groups selected from the group —O—, —C(O)—, —C(O)O—, —S—, —S(O)—, —$SO_2$—, —$SO_3$—, —N=, —N=N—, —NH—, —$NR^1$—, —$PR^1$—, —$P(O)R^1$—, —$P(O)R^1$—O—, —O—P(O) $R^1$—O—, and —$P(R^1)_2$=N—, where $R^1$ is unfluorinated, partially or perfluorinated alkyl having 1-6 C atoms, saturated or partially unsaturated cycloalkyl having 3-10 C atoms, unsubstituted or substituted aryl or saturated or unsaturated, unsubstituted or substituted heterocycle;

X, X' is, identically or differently independently of one another, C, $CR^2$, $SiR^2$, N, P, O or S, where $R^2$ has, identically or differently, the same meaning as R or R', and where $R^2$ may be linked to R or R' to form a 3- to 20-membered ring, and where no radical R or R' is bonded to X or X' if X or X' stands for O or S;

W, W' is, identically or differently independently of one another, C, $CR^3$, $SiR^3$, N, $NR^3$ or P, $PR^3$, where $R^3$ has, identically or differently, the same meaning as R or R', and where the radicals $R^3$ of W and W' may be linked to one another and thus form a bridge;

A is a bridging, saturated or unsaturated unit consisting of one to five bridge atoms, where the bridge atoms are selected from $CR^4$, $CR^4R^5$, N, $NR^4$, P, $PR^4$, O, S, in which $R^4$ and $R^5$ may be identical or different and have, independently of one another, the same meaning as R or R' or are a halogen F, Cl, Br, I, where, in the case of carbon, the unit may optionally be interrupted one or more times at any desired position by heteroatoms N, P, O, S;

Y, Y' is, identically or differently independently of one another, $CR^6$, N, —$CR^6R^7$—, —$SiR^6R^7$—, —$NR^6$—, —$PR^6$—, —$BR^6$—, —$BNR^6$—, —$BNR^6R^7$—, —O— or —S—, where $R^6$ and $R^7$ may be identical or different and have, independently of one another, the same meaning as R or R', or is a bridging unit consisting of one to three bridge atoms, where the bridge atoms are selected from $CR^6$, —$CR^6R^7$—, —$SiR^6R^7$—, —$BR^6$—, —$BNR^6$—, —$BNR^6R^7$—, —$NR^6$—, —$PR^6$—, —O—, —S—, in which $R^6$ has the same meaning as R or R', and where, in the case of carbon, the unit may optionally be interrupted one or more times at any desired position by heteroatoms B, Si, N, P, O, S and/or substituted by $R^6$ and $R^7$ and/or substituted by halogen atoms F, Cl, Br, I, where, in the case of at least 2 C atoms, these may be linked to one another in a saturated or mono- to polyunsaturated manner, and where, in addition, the radicals $R^6$ and/or $R^7$ may be linked to one another, both within Y or Y' and also between Y and Y';

Z, Z' is, identically or differently independently of one another, C, $CR^8$, $SiR^8$, B, N or P, where $R^8$ has, identically or differently, the same meaning as R or R', and where the radicals $R^8$ of Z and Z' may be linked to one another with formation of a ring;

with the proviso that at least one atom from W, X, Y, Z and at least one atom from W', X', Y', Z' contains, identically or independently of one another, a heteroatom selected from Si, B, N, O, S or P;

K, K' is on each occurrence, identically or differently, a mono-, di- or trianionic ligand, which may be mono-, bi, tri-, tetra-, penta- or hexadentate;

L, L' is on each occurrence, identically or differently, a neutral mono-, bi, tri-, tetra-, penta- or hexadentate ligand, o, o' is on each occurrence, identically or differently, the number of ligands K or K' from 0 to 6, where the ligands K and K' may be identical or different in the case of o greater than 1;

p, p' is on each occurrence, identically or differently, the number of ligands L or L' from 0 to 6, where the ligands L and L' may be identical or different in the case of p greater than 1;

where o or o' is selected so that the charge of all ligands K and K' corresponds to the valence of the metal atom employed, and the sum of o and p or o' and p' is dependent on the coordination number of the metal atom employed and the index s and the denticity of the ligand K and L or K' and L', where K or K' may also be weakly coordinating or non-coordinating and, as counterion, balances the charge of the metal complex, where s is an integer from 1 to 3, so that the metal complex contains 1, 2 or 3 biscarbene ligands, which may be identical or different independently of one another, where, depending on the metal atom M and M', ligand $L_p$, $L'_p$, $K_o$, $K'_o$, and steric influences of the biscarbene ligand may also form a very weak or only a coordinative bond to the metal atom.

There is no interaction, a bonding interaction or an antibonding interaction between M and M' in formula (2), and a second carbene ligand may also bond to another metal atom in a bridging manner, so that oligomeric or polymeric structures form.

Furthermore, two or more radicals, which are bonded either to the same atom or to adjacent atoms, may also form an aromatic, heteroaromatic or aliphatic ring system with one another. This applies, for example, to two radicals which are bonded to adjacent atoms in the group A. Aromatic groups A can thus also be formed.

Furthermore, two or more ligands may also be connected to one another via a group R or R' and thus form a tetradentate ligand system or a polypodal ligand.

Again furthermore, the groups R and/or R' may also coordinate to M or M'.

Fully unsaturated substituents in the sense of the present invention are also taken to mean aromatic substituents.

In detail, the collective terms indicated for the various radicals have the following meaning:

Straight-chain or branched alkyl having 1-20 C atoms: straight-chain or branched hydrocarbon radicals having up to 20 C atoms, preferably $C_1$-$C_{12}$-alkyl, such as methyl, ethyl, propyl, isopropyl, n-butyl, sec-butyl, tert-butyl, pentyl, 1-, 2- or 3-methylbutyl, 1,1-, 1,2- or 1,3-dimethylpropyl, 1-ethylpropyl, hexyl, heptyl, octyl, 2-ethylhexyl, nonyl, decyl, undecyl and dodecyl and isomers thereof. Particular preference is given to alkyl radicals having 1-8 C atoms.

Straight-chain or branched alkenyl having 2-20 C atoms and at least one double bond: unsaturated, straight-chain or branched hydrocarbon radicals having at least one double bond in any desired position, preferably $C_2$-$C_{12}$-alkenyl, such as ethenyl, 1- or 2-propenyl, 1-methylethenyl, 1-, 2- or 3-butenyl, 1-methyl-1-propenyl, 1-methyl-2-propenyl, 2-methyl-2-propenyl, 1-, 2-, 3- or 4-pentenyl, 1-, 2-, 3-, 4- or 5-hexenyl, and isomers thereof and the isomers of heptenyl, octenyl, nonenyl, decenyl, undecenyl and dodecenyl. Particular preference is given to alkenyl radicals having 2-8 C atoms.

Straight-chain or branched alkynyl having 2-20 C atoms and at least one triple bond: unsaturated, straight-chain or branched hydrocarbon radicals having at least one triple bond in any desired position, preferably $C_2$-$C_{12}$-alkynyl, such as ethynyl, 1- or 2-propynyl, 1-, 2- or 3-butynyl, 1-methyl-2-propynyl, 1-, 2-, 3- or 4-pentynyl, 1-, 2-, 3-, 4- or 5-hexynyl, and isomers thereof and the isomers of heptynyl, octynyl, nonynyl, decynyl, undecynyl and dodecynyl. Particular preference is given to alkynyl radicals having 2-8 C atoms.

Saturated, partially or fully unsaturated cycloalkyl having 3 to 10 C atoms, which may be substituted by alkyl groups having 1 to 10 C atoms: mono-cyclic, saturated, partially or fully unsaturated, i.e. aromatic hydrocarbon group having 3 to 10 carbon ring members, preferably having 3 to 7 carbon ring members, such as cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$-$C_{10}$-alkyl groups.

The individual substituents may, as described above, be partially or fully substituted by halogen or partially substituted by CN or $NO_2$, independently of one another, at any desired position, where halogen is selected from the group consisting of F, Cl, Br and I. The number of halogen atoms in a substituent is preferably a maximum of 19, particularly preferably a maximum of 9, very particularly preferably a maximum of 3, and in particular the substituent is not substituted by halogen atoms. The number of CN and $NO_2$ groups in a substituent is preferably a maximum of 4, particularly preferably 1, and in particular the substituent is not substituted by CN or $NO_2$ groups.

In accordance with the invention, a carbon atom of one or more substituents R and R' may be replaced by atoms and/or atom groups selected from the group —O—, —C(O)—, —C(O)O—, —S—, —S(O)—, —$SO_2$—, —$SO_3$—, —N=, —N=N—, —NH—, —$NR^1$—, —$PR^1$—, —$P(O)R^1$, —$P(O)R^1$—O—, —O—$P(O)R^1$—O—, and —$P(R^1)_2$=N—, where $R^1$ is unfluorinated, partially or perfluorinated alkyl having 1-6 C atoms, saturated or partially or fully unsaturated cycloalkyl having 3-7 C atoms, unsubstituted or substituted phenyl or unsubstituted or substituted heterocycle, where the terms alkyl and cycloalkyl have the meaning given above. The heterocycle from $R^1$ preferably stands for five- to nine-membered, in particular five- to six-membered ring systems containing oxygen, nitrogen and/or sulfur atoms, such as, for example, 2- or 3-furyl, 2- or 3-thienyl, 1-, 2- or 3-pyrrolyl, 1-, 2-, 4- or 5-imidazolyl, 3-, 4- or 5-pyrazolyl.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neo-pentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcycloheptyl, n-octyl, 2-ethylhexyl, cyclo-octyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, cis- or trans-monobenzoindenofluorene, cis- or trans-dibenzoindeno-fluorene, truxene, isotruxene, spirotruxene, spiroisotruxene, furan, benzo-furan, isobenzofuran, dibenzofuran, thiophene, benzothiophene, isobenzo-thiophene, dibenzothiophene, pyrrole, indole, isoindole, carbazole, indolo-carbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazin-imidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preferred embodiments of the compounds of the formulae (1), (2) and (3) are described below.

X, X' have, identically or differently independently of one another, the meaning C, $CR^2$, $SiR^2$, N, P, O or S, where $R^2$ has, identically or differently, the same meaning as R and R', preferably C, $CR^2$, N, P, O, or S, particularly preferably $CR^2$, N and S, and where $R^2$ may be linked to R or R' to form a 3- to 20-membered ring, preferably to form a 3- to 12-membered ring, particularly preferably to form a 5- to 8-membered ring. If X or X' stands for O or S, no radical R or R' is bonded to these groups. X and X' is very particularly preferably, identically or differently on each occurrence, $CR^2$ or N, in particular N.

A double bond is preferably formally present in each case between W and Y and between W' and Y', i.e. a double bond can be drawn in the Lewis notation. This is the case, for example, if W stands for C and Y stands for $CR^6$ or N.

W, W' have, identically or differently independently of one another, the meaning C, $CR^3$, $SiR^3$, N or P, where $R^3$ has, identically or differently, the same meaning as R and R', preferably C, $CR^3$, N, P, particularly preferably C, $CR^3$, and where the radicals $R^3$ of W and W' may also be linked to one another and thus form a bridge, which preferably consists of 1 to 6 bridge atoms, particularly preferably of 2 to 4 bridge atoms. W and W' very particularly preferably stand for C.

A has the meaning of a bridging unit consisting of one to five bridge atoms, preferably one, two or three bridge atoms, particularly preferably two bridge atoms. The unit may be saturated or unsaturated, in particular it is unsaturated. The bridge atoms are selected from C, $-CR^4-$, $-CR^4R^5-$, N, $-NR^4-$, P, $-PR^4-$, $-O-$, $-S-$, in which $R^4$ and $R^5$ may be identical or different and have, independently of one another, the same meaning as R or R' or are a halogen. The bridge atoms are preferably C, $-CR^4-$, $-CR^4R^5-$, N, $-NR^4-$, $-O-$, $-S-$, particularly preferably $CR^4$, N, and where, in the case of carbon, the unit may optionally be interrupted one or more times at any desired position by heteroatoms N, P, O, S, preferably N, O, S. Particularly preferred groups A are $-CR^4=CR^4-$, $-CR^4=N-$ and $-CR^4R^5-CR^4R^5-$, very particularly preferably $-CR^4=CR^4-$ and $-CR^4=N-$, in particular $-CR^4=CR^4-$. If the radicals $R^4$ form a ring with one another, the formation of an aryl or heteroaryl group is also possible. A further preferred group A is an optionally substituted ortho-phenylene group.

Y, Y' have, identically or differently independently of one another, the meaning $CR^6$, N, $CR^6R^7$, $SiR^6R^7$, $NR^6$, $PR^6$, $BR^6$, $BNR^6$, $BNR^6R^7$, O or S, where $R^6$ and $R^7$ may be identical or different and have, independently of one another, the same meaning as R and R'. Y and Y' preferably have the meaning $CR^6$, N, $CR^6R^7$, $NR^6$, $PR^6$, $BR^6$, $BNR^6$, $BNR^6R^7$, particularly preferably $CR^6$, N, $CR^6R^7$, $NR^6$. Y and Y' forms a bridging unit consisting of up to three bridge atoms, where the bridge atoms are selected from carbon and/or the heteroatoms, where, in the case of heteroatoms, the unit consists of up to three heteroatoms as bridge atom and is selected from $-BR^6-$, $BNR^6-$, $BNR^6R^7-$, $SiR^6R^7$, $-NR^6-$, $-PR^6-$, $-O-$, $-S-$, in which $R^6$ has, identically or differently, the same meaning as R and R', preferably from $BR^6$, $BNR^6$, $BNR^6R^7$, $-NR^6-$, in particular $-NR^6-$, and where, in the case of carbon, the unit consists of up to three carbon atoms as bridge atoms, preferably 1 or 2, particularly preferably 1, which may optionally be interrupted one or more times at any desired position by heteroatoms B, N, P, O, S and/or substituted by $R^3$ and $R^4$ and/or substituted by halogen atoms F, Cl, Br, I, where, in the case of at least one C atoms, these may be linked to one another in a saturated or mono- to polyunsaturated manner, and where, in addition, the radicals $R^6$ and/or $R^7$ may be linked to one another between Y and Y'.

Y and Y' are particularly preferably, identically or differently on each occurrence, $CR^6$ or N, where these groups then in each case form a double bond to the adjacent group W or W', very particularly preferably $CR^6$.

Z, Z' have, identically or differently independently of one another, the meaning C, $CR^8$, $SiR^8$, B, N or P, where $R^8$ has, identically or differently, the same meaning as R and R'; Z and Z' preferably have the meaning C, $CR^8$, N and P, particularly preferably C and N, and where the radicals $R^8$ of Z and Z' may be linked to one another with formation of a ring, which preferably consists of 3 to 8 ring atoms, particularly preferably of 3 to 6 ring atoms. Z and Z are very particularly preferably equal to N.

Furthermore, it is essential to the invention that at least one atom from W, X, Y, Z and at least one atom from W', X', Y', Z' contains, identically or independently of one another, a heteroatom selected from Si, B, N, O, S or P. X, X', Z, Z' and/or Y, Y' are preferably heteroatoms, particularly preferably X, X' and Z, Z. In a particularly preferred embodiment of the invention, X, X' and Z, Z' are nitrogen.

M and M' are preferably selected, identically or differently on each occurrence, from the group consisting of Fe, Ru, Os, Co, Rh, Ir, Ni, Pd, Pt, Cu, Ag, Au, Ti, Zr, V, Mn, Sc, Cr, Mo, W and Al, particularly preferably Ni, Pd, Pt, Cu, Ag, Au, Fe, Ru, Os, Co Rh and Ir and very particularly preferably Ir, Pt and Cu.

R and R' are preferably selected, identically or differently on each occurrence, from the group consisting of straight-chain or branched alkyl having 1-10 C atoms, straight-chain or branched alkenyl having 2-10 C atoms and at least one double bond, saturated, partially or fully unsaturated cycloalkyl having 3-8 C atoms, which may be substituted by alkyl groups having 1-10 C atoms, unsubstituted or substituted aryl or aromatic ring system, unsubstituted or substituted heterocycle or heteroaromatic ring system or substituted or unsubstituted aralkyl or heteroaralkyl, where one or both substituents R and R' may be partially substituted in any desired position or fully substituted by F, and where a carbon atom of one or both substituents R and R' may be replaced by atoms and/or atom groups selected from the group —O—, —C(O)—, —C(O)O—, —S—, —NR$^1$—, —PR$^1$— or —P(O)R'—, where R$^1$ is unfluorinated, partially or perfluorinated alkyl having 1-6 C atoms, saturated or partially unsaturated cycloalkyl having 3-10 C atoms, unsubstituted or substituted aryl or saturated or unsaturated, unsubstituted or substituted heterocycle.

R and R' are particularly preferably selected, identically or differently on each occurrence, from the group consisting of straight-chain or branched alkyl having 1-10 C atoms, saturated cycloalkyl having 3-6 C atoms, which may be substituted by alkyl groups having 1-4 C atoms, unsubstituted or substituted aryl or aromatic ring system, unsubstituted or substituted heterocycle or heteroaromatic ring system or substituted or unsubstituted aralkyl or heteroaralkyl, and where a carbon atom of one or both substituents R and R' may be replaced by —O—.

If R or R' is coordinated to the metal, R or R' preferably stands for a substituted or unsubstituted aralkyl or heteroaralkyl group and in particular for a —CH$_2$—CH$_2$-aryl or —CH$_2$—CH$_2$-heteroaryl group, where aryl or heteroaryl and/or the CH$_2$ groups may each also be substituted and preferred substituents are alkyl groups having 1 to 5 C atoms or aromatic or heteroaromatic ring systems which are optionally substituted by alkyl groups. Furthermore, one of the CH$_2$ groups may also be substituted by O, S or NR. Furthermore suitable for this purpose are also aryl or heteroaryl groups coordinating the groups, which are in each case bonded to X or X' via an optionally substituted ortho-arylene or ortho-heteroarylene group.

The above-mentioned embodiments can be combined with one another as desired. The above-mentioned preferred embodiments preferably occur simultaneously.

Preferred embodiments of the compounds of the formulae (1), (2) and (3) are therefore the compounds of the following formulae (1a), (2a) and (3a) respectively,

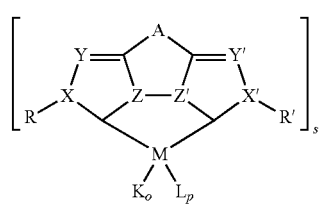

formula (1a)

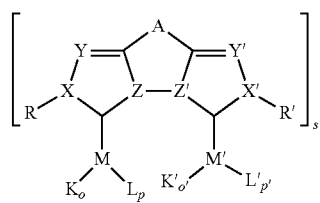

formula (2a)

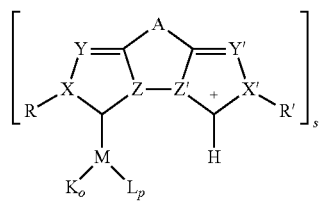

formula (3a)

where R, R', R$^1$ to R$^8$, K, K', L, L', o, o', p, p' and s have the meanings given above and the other symbols and indices used have the following meanings:

M, M' is selected on each occurrence, identically or differently, from the group consisting of Fe, Ru, Os, Co, Rh, Ir, Ni, Pd, Pt, Cu, Ag, Au, Ti, Zr, V, Mn, Sc, Cr, Mo and W;

X, X' is, identically or differently independently of one another, CR$^2$ or N;

A is —CR$^4$═CR$^4$—, —CR$^4$═N— or —CR$^4$R$^5$—CR$^4$R$^5$—;

Y, Y' is, identically or differently independently of one another, CR$^6$ or N;

Z, Z' is, identically or differently independently of one another, CR$^8$ or N;

with the proviso that at least one atom from W, X, Y, Z and at least one atom from W', X', Y', Z' contains, identically or independently of one another, a nitrogen atom.

Particularly preferred embodiments of the compounds of the formulae (1), (2) and (3) are therefore the compounds of the following formulae (1b), (2b) and (3b) respectively,

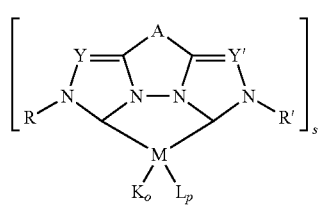

formula (1b)

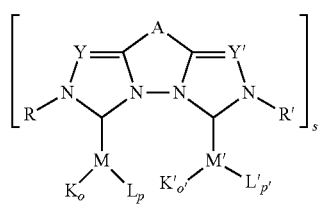

formula (2b)

formula (3b)

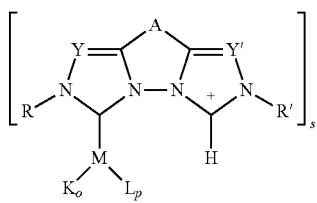

formula (2d)

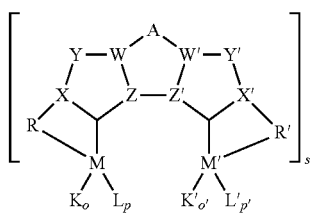

formula (3c)

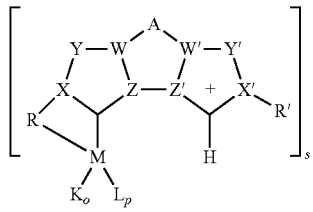

where R, R', R¹ to R⁸, K, K', L, L', o, o', p, p' and s have the meanings given above and the other symbols and indices used have the following meanings:

M, M' is selected on each occurrence, identically or differently, from the group consisting of Ir, Pt and Cu;

A is $-CR^4=CR^4-$ or $-CR^4=N-$, preferably $-CR^4=CR^4-$;

Y, Y' is, identically or differently independently of one another, $CR^6$ or N;

Z, Z' is, identically or differently independently of one another, $CR^8$ or N, preferably N.

Preferred examples of metal complexes of the formulae (1), (2) and (3) according to the invention are characterised in that X, X', Z, Z' are equal to nitrogen, Y, Y' are equal to $-CH=$, W, W' are equal to carbon, A is equal to $-CH=CH-$, R, R' are equal to alkyl, in particular methyl, ethyl, n-propyl, i-propyl or tert-butyl, M, M' are equal to $Pt^{2+}$, $Ir^+$, $Ir^{3+}$, $Pd^{2+}$, $Cu^+$, $Ag^+$, $Au^+$ or $Rh^+$, K, K' are equal to iodide (in the case of $Pd^{2+}$), $PF_6^-$ (in the case of $Cu^+$, $Ag^+$, $Au^+$), L, L' are equal to CO, COD (in the case of $Rh^+$) and s is equal to 1 in the case of $Pd^{2+}$, $Rh^+$ and s is equal to 2 in the case of $Cu^+$, $Ag^+$, $Au^+$.

As described above, it is also possible for the radicals R and/or R' to coordinate to the metal or metals. This is depicted diagrammatically for the compounds of the following formulae (1c), (1d), (2c), (2d) and (3c), formula (1c)

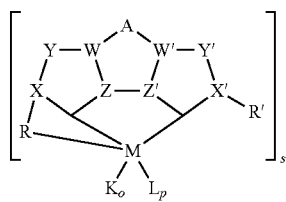

formula (1d)

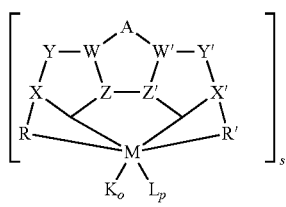

formula (2c)

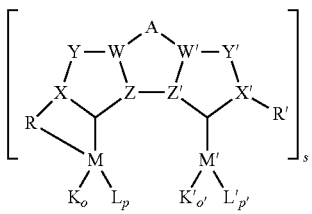

where the symbols and indices used have the meanings given above.

Furthermore, as described above, two or more of the ligands may be connected to one another by a bridging group, i.e. a group R or R' connects two or more ligands, so that overall a tetradentate or polypodal ligand thereby forms. Suitable groups which can be used as bridging groups are known to the person skilled in the art and can also be used for the ligands mentioned here without inventive step.

Suitable monoanionic ligands K and K' may be mono-, bi-, tri-, tetra-, penta- or hexadentate, selected from the group consisting of hydride, deuteride, the halides F, Cl, Br and I, pseudohalides, azide, trifluoro-sulfonates, alkylacetylides, such as, for example, methyl-C≡C⁻, tert-butyl-C≡C⁻, aryl- or heteroarylacetylides, such as, for example, phenyl-C≡C⁻, alkyl groups which are linked to the metal atom M via a σ bond, such as, for example, methyl, ethyl, n-propyl, i-propyl, n-butyl, s-butyl, t-butyl, alkyl-aryl radicals which are linked to the metal atom M via a σ bond, aryl groups, such as, for example, phenyl, naphthyl, heteroaryl, such as, for example, pyridyl, hydroxide, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, anionic, nitrogen-containing heterocycles, such as, for example, pyrrolide, imidazolide, pyrazolide, aliphatic and aromatic phosphides $PR_2^-$, aliphatic or aromatic selenides $SeR^-$, cyclopentadienyl (Cp), where the cyclopentadienyl groups may be substituted by alkyl substituents, preferably methyl or tert-butyl, particularly preferably by five methyl groups, so that the substituted cyclopentadienyl radical denotes pentamethylcyclopentadienyl (Cp*), or indenyl, where the indenyl radical may optionally be substituted by alkyl substituents, preferably methyl. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. Suitable di- or trianionic ligands K and K' are $O^{2-}$, $S^{2-}$, nitrenes, which result in coordination in the form R—N=M, where R generally stands for a substituent, or $N^{3-}$.

The ligand K is particularly preferably selected from the group consisting of halides, pseudohalides, alcoholates, carboxylates, acetylacetonate and derivatives thereof, trifluorosulfonate, alkynyl groups, aryl groups and heteroaryl groups.

Suitable mono- or dianionic bidentate ligands K and K' are selected from 1,3-diketonates derived from 1,3-diketones, such as, for example, acetyl-acetone, tert-butylacetylacetone (2,2,6,6-tetramethyl-3,5-heptanedione), benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylamino-alanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preference is furthermore given to bidentate monoanionic or dianionic ligands K and K', which, with the metal, have a cyclometallated five-membered ring or six-membered ring having at least one metal-carbon bond or having two metal-nitrogen bonds, in particular a cyclometallated five-membered ring. These are, in particular, ligands as are generally used in the area of phosphorescent metal complexes for organic electroluminescent devices, i.e. ligands of the phenylpyridine, naphthylpyridine, phenyl-quinoline, phenylisoquinoline, etc., type, each of which may be substituted by one or more radicals $R^1$. A multiplicity of ligands of this type is known to the person skilled in the art in the area of phosphorescent electroluminescent devices, and he will be able to select further ligands of this type as ligand K or K' for compounds of the formula (1), (2) or (3) without inventive step. In general, the combination of two groups, as are represented by the following formulae (A) to (BB), is particularly suitable for this purpose. In general, combinations which are bonded via a neutral nitrogen atom or a carbene atom and via a negatively charged carbon atom or a negatively charged nitrogen atom, but also combinations in which, for example, two neutral nitrogen atoms or two negative charged nitrogen atoms or two negatively charged carbon atoms are bonded to the metal, are suitable for this purpose. The bidentate ligand K or K' can then be formed from the groups of the formulae (A) to (BB) through these groups being bonded to one another in each case at the position denoted by #. The position at which the groups coordinate to the metal is denoted by *.

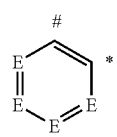

formula (A)

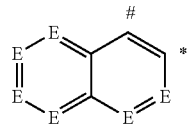

formula (B)

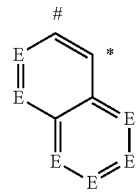

formula (C)

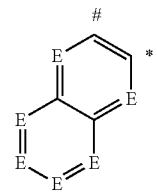

formula (D)

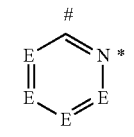

formula (E)

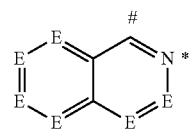

formula (F)

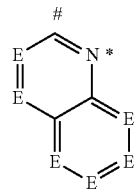

formula (G)

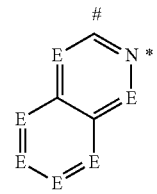

formula (H)

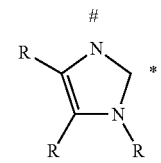

formula (I)

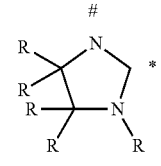

formula (J)

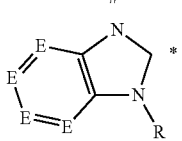

formula (K)

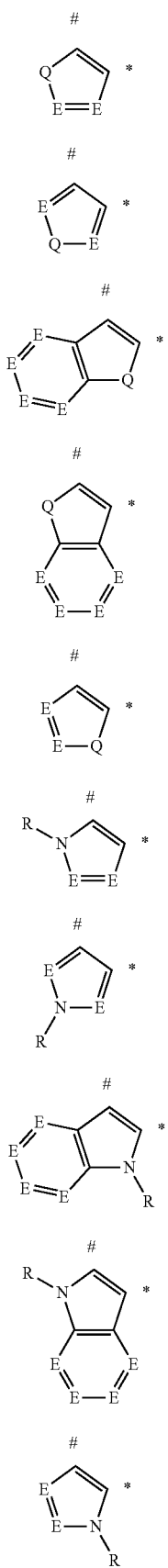
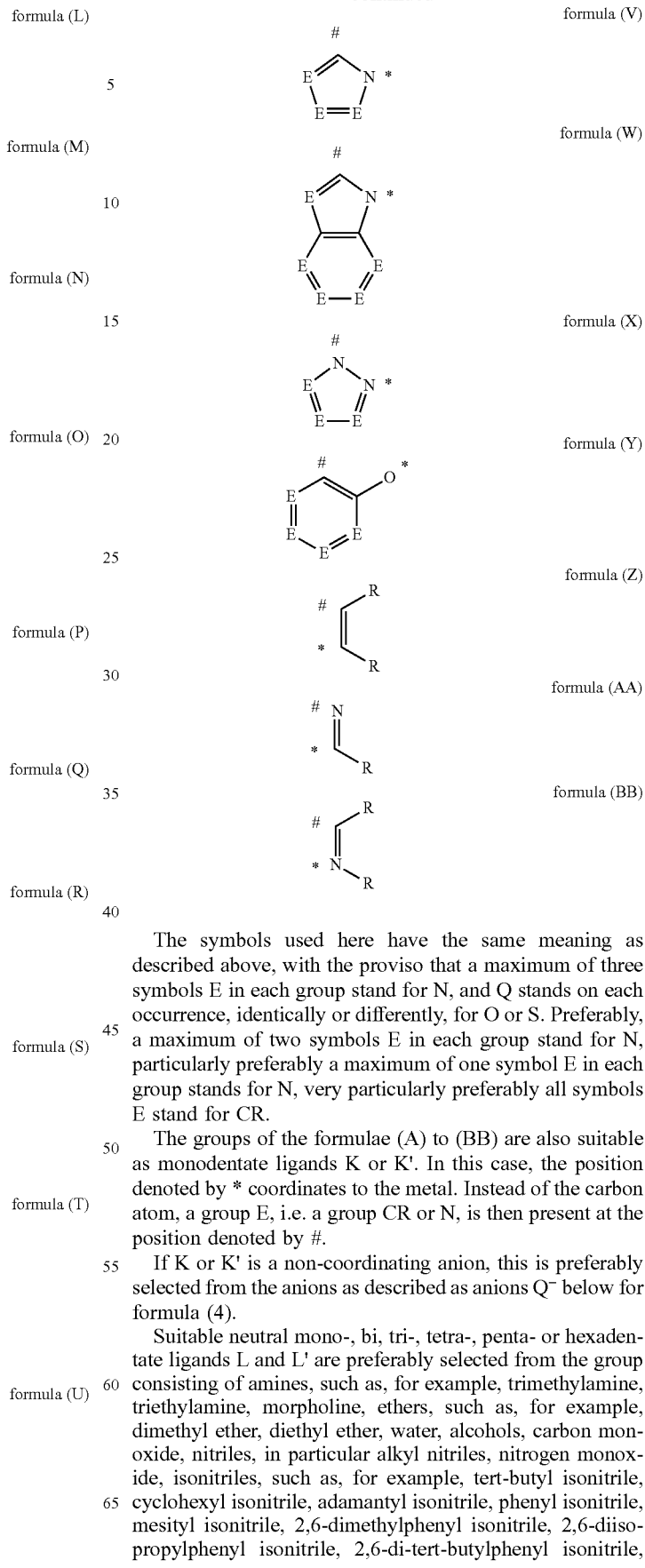

The symbols used here have the same meaning as described above, with the proviso that a maximum of three symbols E in each group stand for N, and Q stands on each occurrence, identically or differently, for O or S. Preferably, a maximum of two symbols E in each group stand for N, particularly preferably a maximum of one symbol E in each group stands for N, very particularly preferably all symbols E stand for CR.

The groups of the formulae (A) to (BB) are also suitable as monodentate ligands K or K'. In this case, the position denoted by * coordinates to the metal. Instead of the carbon atom, a group E, i.e. a group CR or N, is then present at the position denoted by #.

If K or K' is a non-coordinating anion, this is preferably selected from the anions as described as anions $Q^-$ below for formula (4).

Suitable neutral mono-, bi, tri-, tetra-, penta- or hexadentate ligands L and L' are preferably selected from the group consisting of amines, such as, for example, trimethylamine, triethylamine, morpholine, ethers, such as, for example, dimethyl ether, diethyl ether, water, alcohols, carbon monoxide, nitriles, in particular alkyl nitriles, nitrogen monoxide, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, olefins, nitrogen-containing heterocycles, such as, for example, pyridine, pyridazine, pyrazine, pyrimidine, triazine, where each of these may be substituted by alkyl or aryl groups, phosphines, preferably trialkyl-, triaryl or alkylarylphosphines, particularly preferably PAr$_3$, where Ar is a substituted or unsubstituted aryl radical and the three aryl radicals in PAr$_3$ may be identical or different, such as, for example, PPh$_3$, PMe$_3$, PEt$_3$, P(n-Bu)$_3$, P(t-Bu)$_3$, PEt$_2$Ph, PMe$_2$Ph, P(n-Bu)$_2$Ph, PAd$_3$, PMeAd$_2$, PCy$_3$, PF$_3$, tris(pentafluoro-phenyl)phosphine, phosphonates and derivatives, arsenates thereof and derivatives thereof, phosphites, such as, for example, trimethyl phosphite, triethyl phosphite, arsines, such as, for example, trifluoroarsine, trimethylarsine, tricyclohexylarsine, tri-tert-butylarsine, triphenylarsinine, tris(penta-fluorophenyl)arsine, stibines, such as, for example, trifluorostibine, trimethylstibine, tricyclohexylstibine, tri-tert-butylstibine, triphenylstibine, tris(pentafluorophenyl)stibine, aliphatic or aromatic sulfides, such as, for example, dimethyl sulfide, diethyl sulfide, or aliphatic or aromatic selenides, such as, for example, dimethyl selenide, diethyl selenide, carbenes and acetylenically unsaturated multiple-bond systems.

Suitable neutral bidentate ligands L and L' are furthermore selected from diamines, such as, for example, ethylenediamine, N,N,N',N'-tetramethyl-ethylenediamine, propylenediamine, N,N,N',N'-tetramethylpropylenedi-amine, cis- or trans-diaminocyclohexane, cis- or trans-N,N,N',N'-tetra-methyldiaminocyclohexane, imines, such as, for example, 2-[1-(phenyl-imino)ethyl]pyridine, 2-[1-(2-methylphenylimino)ethyl]pyridine, 2-[1-(2,6-diisopropylphenylimino)ethyl]pyridine, 2-[1-(methylimino)ethyl]pyridine, 2-[1-(ethylimino)ethyl]pyridine, 2-[1-(isopropylimino)ethyl]pyridine, 2-[1-(tert-butylimino)ethyl]pyridine, diimines, such as, for example, 1,2-bis-(methylimino)ethane, 1,2-bis(ethylimino)ethane, 1,2-bis(isopropylimino)-ethane, 1,2-bis(tert-butylimino)ethane, 2,3-bis(methylimino)butane, 2,3-bis(ethylimino)butane, 2,3-bis(isopropylimino)butane, 2,3-bis(tert-butyl-imino)butane, 1,2-bis(phenylimino)ethane, 1,2-bis(2-methylphenylimino)-ethane, 1,2-bis(2,6-diisopropylphenylimino)ethane, 1,2-bis(2,6-di-tert-butylphenylimino)ethane, 2,3-bis(phenylimino)butane, 2,3-bis(2-methyl-phenylimino)butane, 2,3-bis(2,6-diisopropylphenylimino)butane, 2,3-bis-(2,6-di-tert-butylphenylimino)butane, heterocycles containing two nitrogen atoms, such as, for example, 2,2'-bipyridine, o-phenanthroline, and diphosphines, such as, for example, bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis(dimethylphosphino)propane, bis(dimethylphosphino)-butane, bis(diethylphosphino)methane, bis(diethylphosphino)ethane, bis(diethylphosphino)propane, bis(diethylphosphino)butane, bis(di-tert-butylphosphino)methane, bis(di-tert-butylphosphino)ethane, bis(tert-butyl-phosphino)propane, bis(tert-butylphosphino)butane, and conjugated dienes which form a p-complex with the metal atom M, preferably η$^4$-1,3-butadiene, η$^4$-diphenyl-1,3-butadiene, η$^4$-1,3-pentadiene, η$^4$-1-phenyl-1,3-pentadiene, η$^4$-1,4-dibenzyl-1,3-butadiene, η$^4$-2,4-hexadiene, η$^4$-3-methyl-1,3-pentadiene, η$^4$-1,4-ditolyl-1,3-butadiene, η$^4$-1,4-bis(trimethylsilyl)-1,3-butadiene and η$^2$- or η$^4$-cyclooctadiene (COD) (each 1,3 and each 1,5), particularly preferably η$^4$-1,4-diphenyl-1,3-butadiene, η$^4$-1-phenyl-1,3-pentadiene, η$^4$-2,4-hexadiene, butadiene, η$^4$-1,3-cyclooctadiene and η$^2$-1, 5-cyclooctadiene.

Particular preference is given to the use of neutral mono-, bi-, tri-, tetra-, penta- or hexadentate phosphorus-free ligands selected from the group consisting of amines, ethers water, alcohols, pyridines, where the pyridines may be substituted by alkyl or aryl groups, carbon monoxide, nitriles, preferably alkyl nitriles, olefins, preferably ethylene, cyclooctene, η$^4$-1,4-diphenyl-1,3-butadiene, η$^4$-1-phenyl-1,3-pentadiene, η$^4$-2,4-hexadiene, butadiene, η$^4$-1,3-cyclooctadiene and η$^2$-1,5-cyclooctadiene.

Examples of suitable metal complexes according to the invention are the compounds shown in the following table.

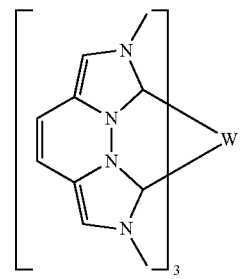

1

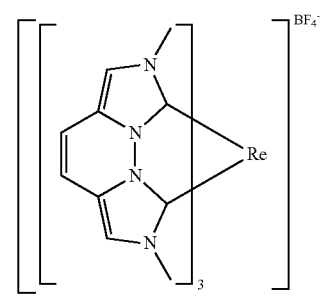

2

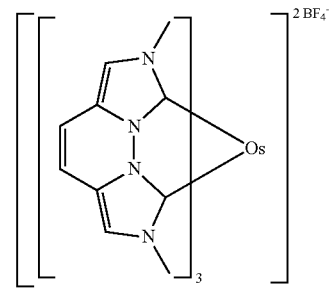

3

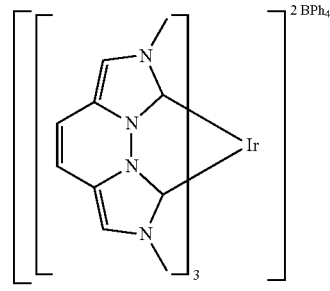

4

| 19 -continued | 20 -continued |
|---|---|
| 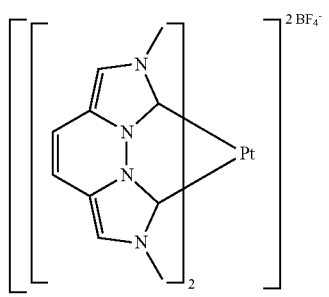 5 | 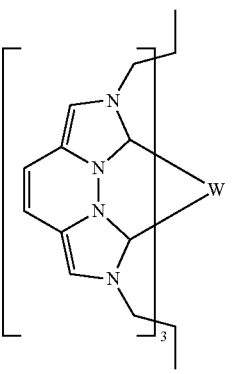 10 |
| 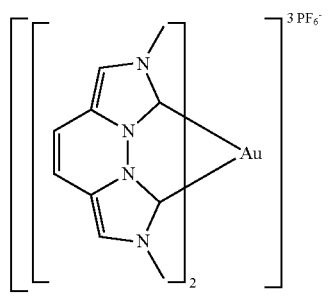 6 | 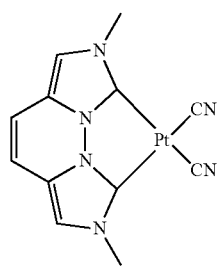 11 |
| 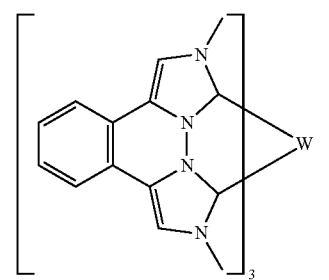 7 | 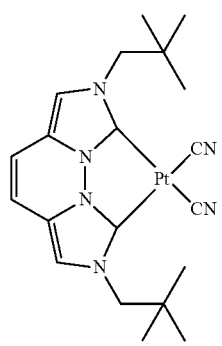 12 |
| 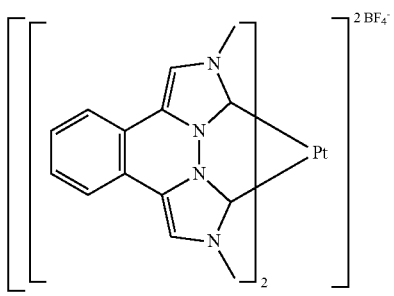 8 | 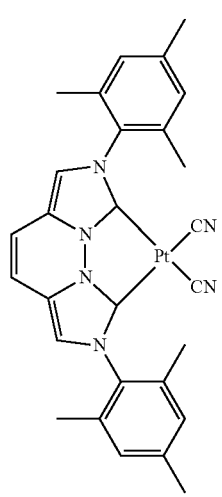 13 |
| 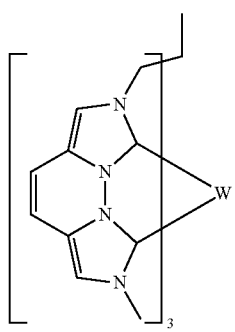 9 | |

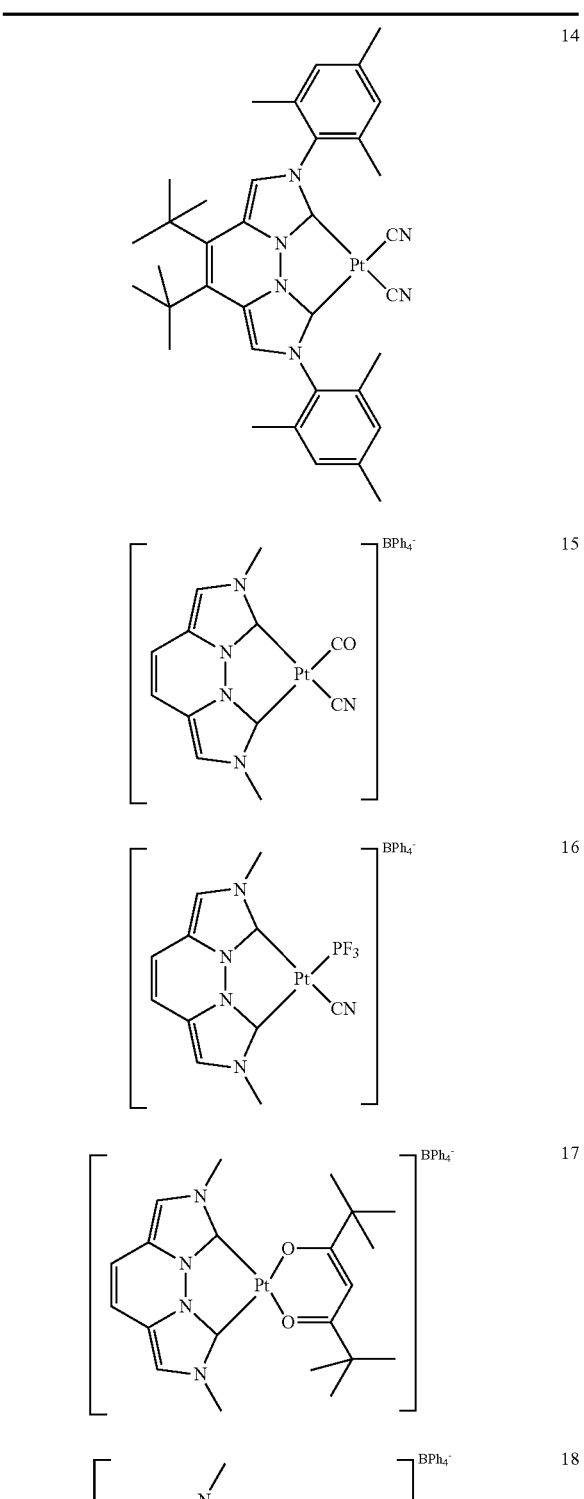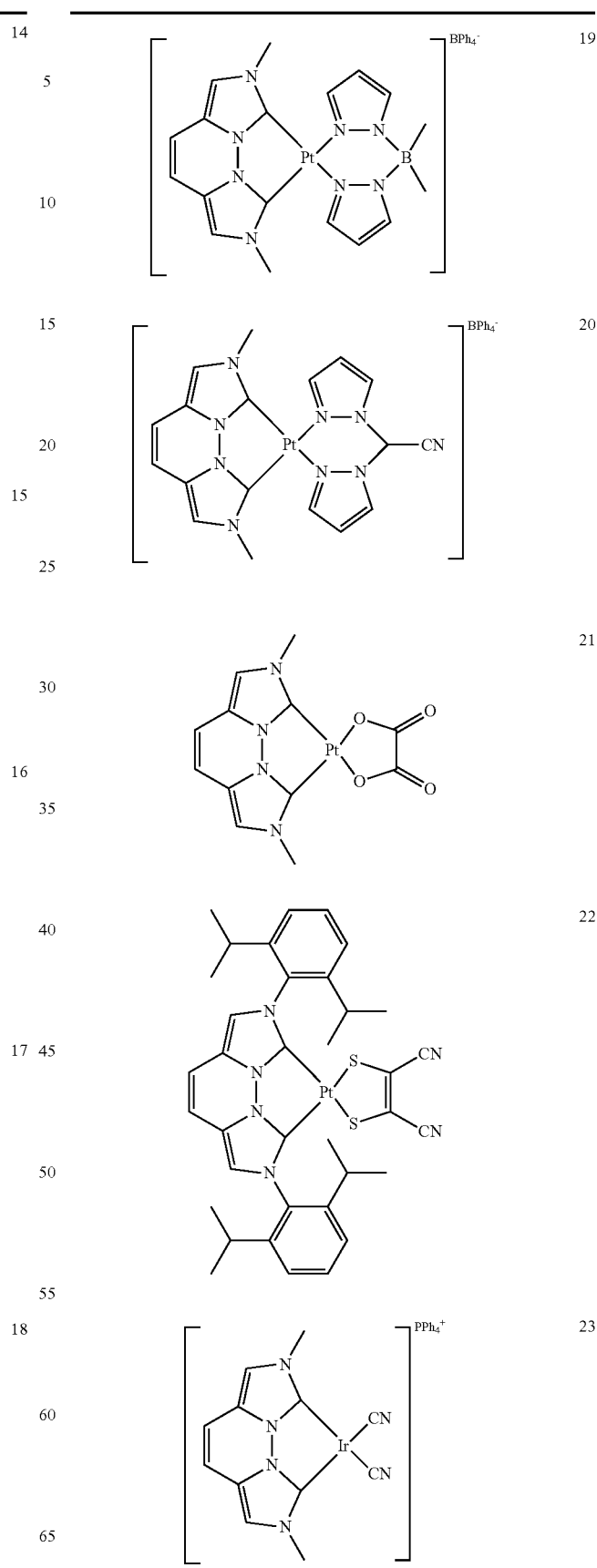

24
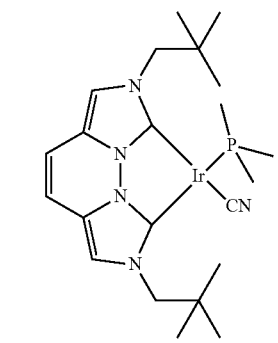
25
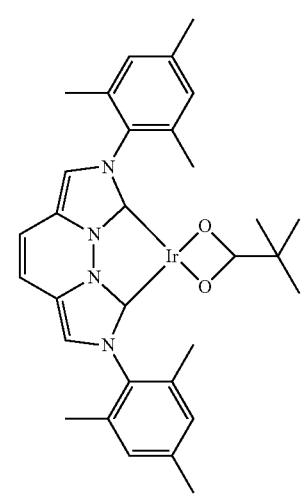
26
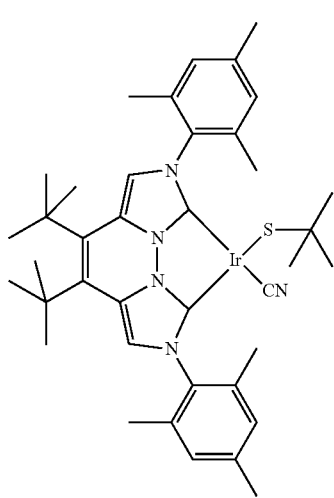
27
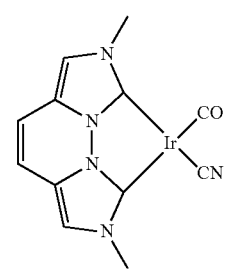
28
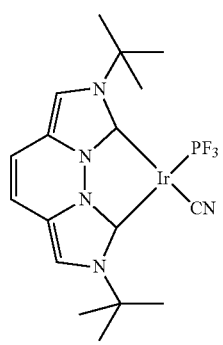
29
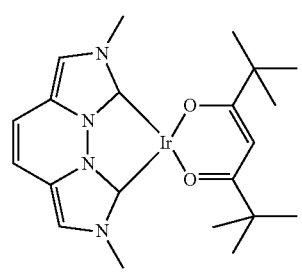
30
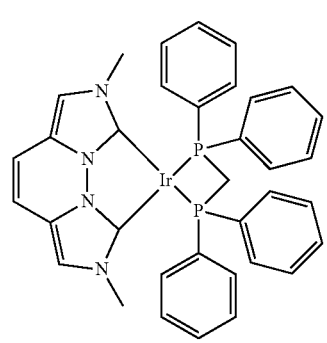
31
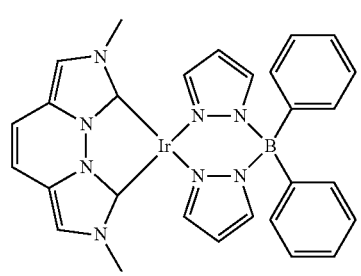
32
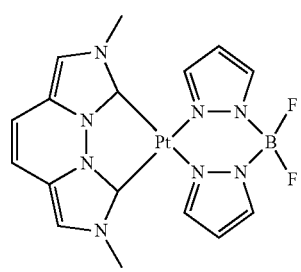

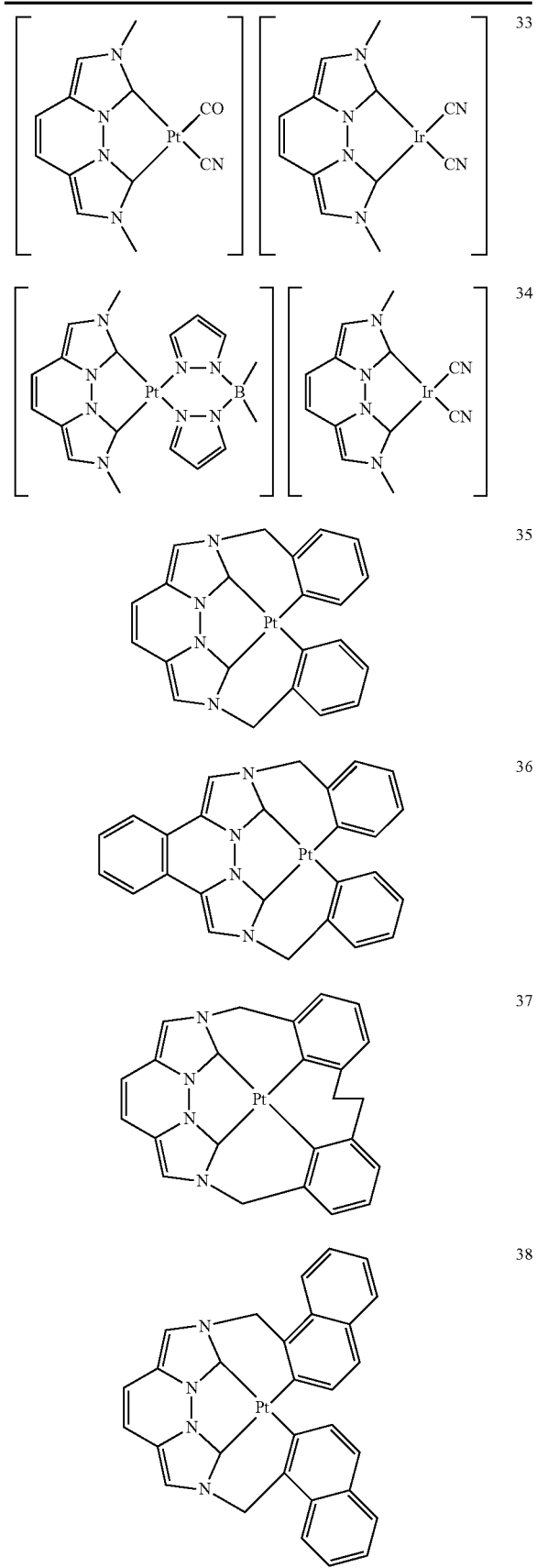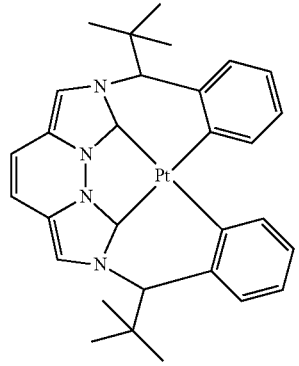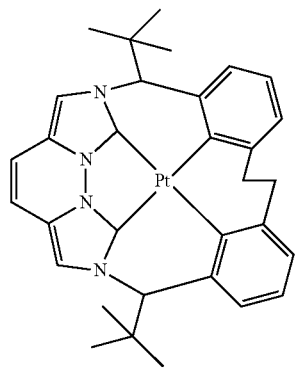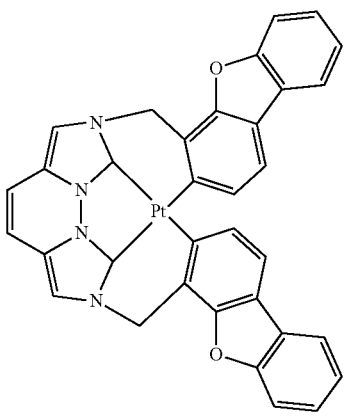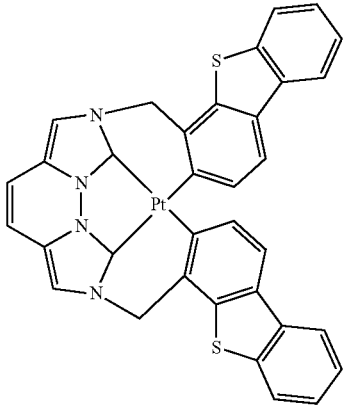

| | |
|---|---|
| 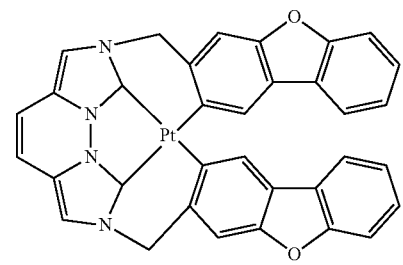 43 | 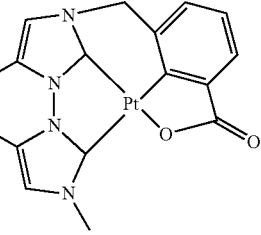 50 |
| 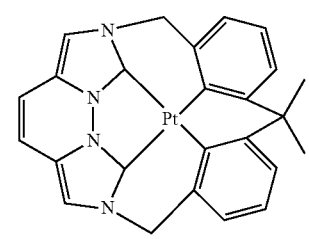 44 | 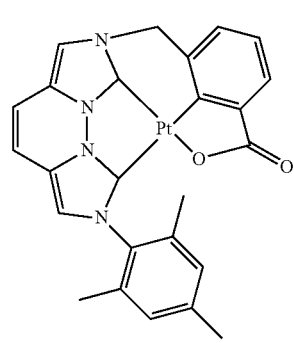 51 |
| 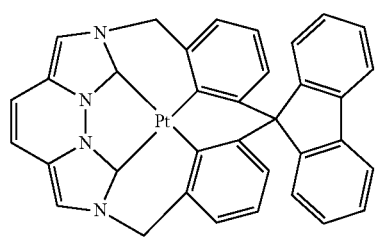 45 | |
| 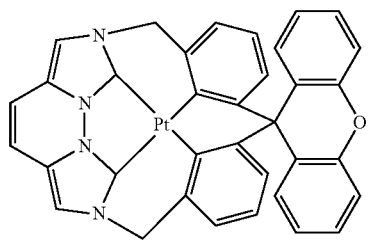 46 | 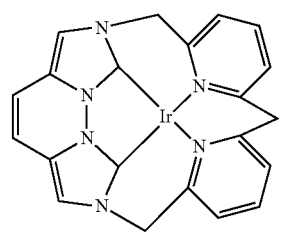 52 |
| 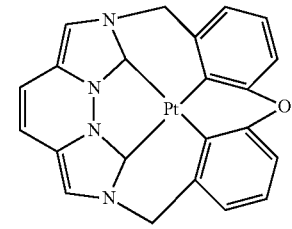 48 | 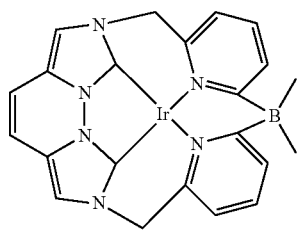 53 |
| 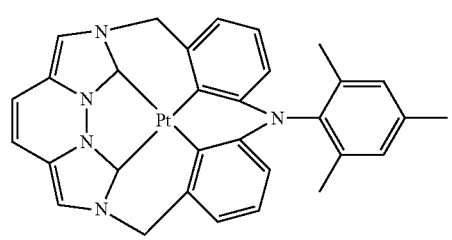 49 | 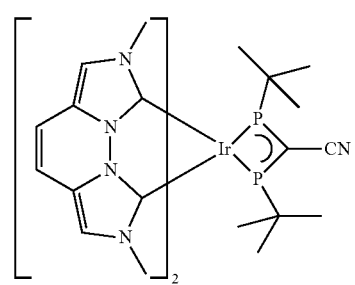 54 |

| 29 -continued | 30 -continued |
|---|---|
| 55 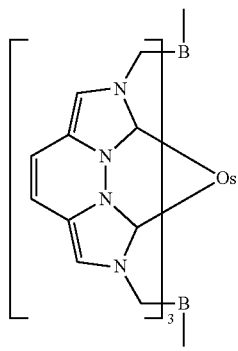 | 59 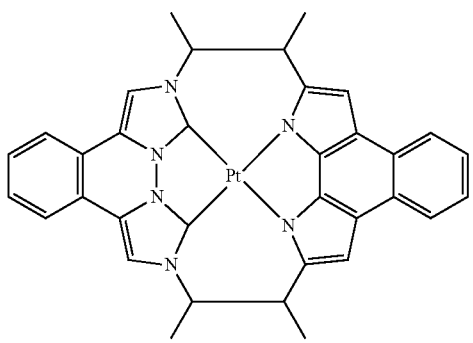 |
| 56 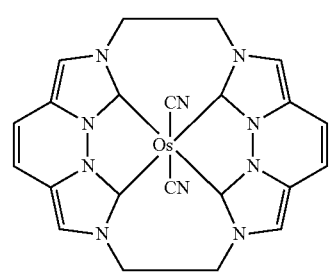 | 60 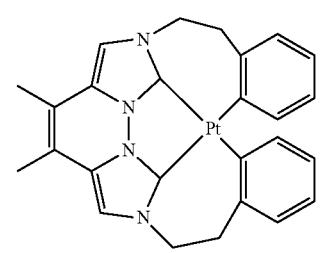 |
| 57 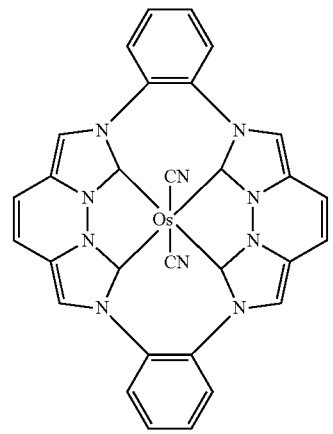 | 61 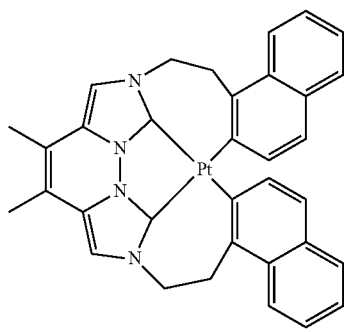 |
|  | 63 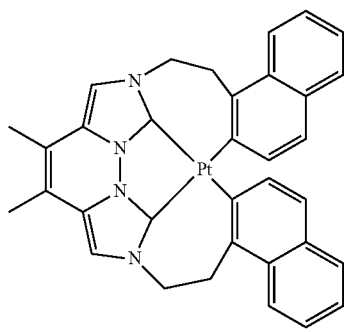 |
| 58 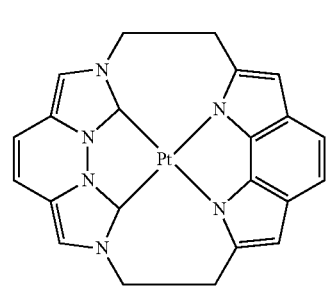 | 64 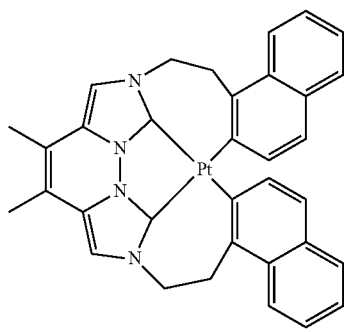 |

65 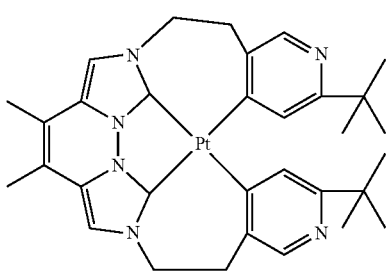

66 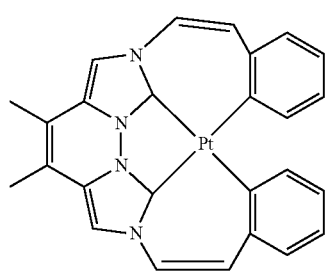

67 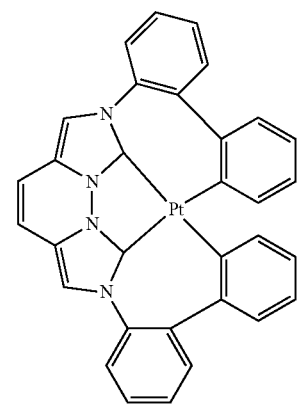

68 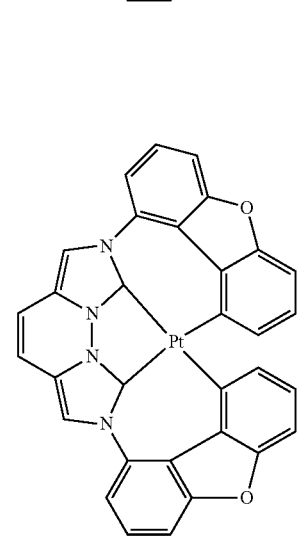

69 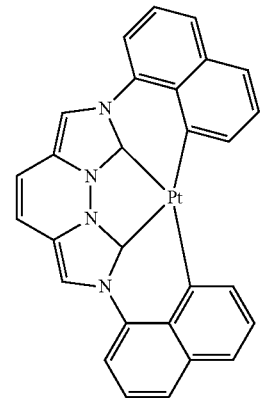

70 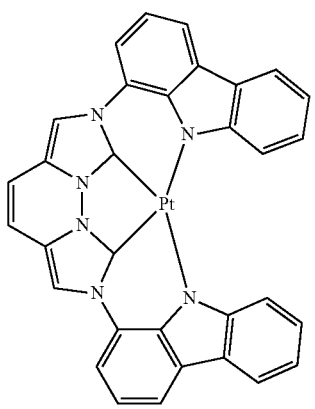

The compounds according to the invention can also be rendered soluble by suitable substitution, for example by relatively long alkyl groups (about 4 to 20 C atoms), in particular branched alkyl groups, or optionally substituted aryl groups, for example xylyl, mesityl or branched terphenyl or quater-phenyl groups. Compounds of this type are then soluble in common organic solvents, such as, for example, toluene or xylene, at room temperature in adequate concentration in order to be able to process the complexes from solution. These soluble compounds are particularly suitable for processing, for example, by printing processes.

The present invention therefore furthermore relates to a formulation, in particular a solution, a suspension or a mini-emulsion, comprising at least one compound of the formula (1), (2) or (3) or the preferred embodiments indicated above and at least one solvent.

The present invention furthermore relates to the ligands on which the compounds of the formula (1) to (3) are based, as corresponding bisimidazolium salts and the biscarbenes derived therefrom.

The invention therefore furthermore relates to compounds of the formula (4) and the biscarbene of the formula (5) derived therefrom, formula (4)

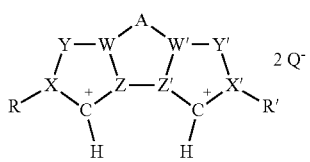

-continued

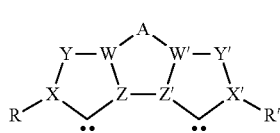

formula (5)

where R, R', X, X', W, W', A, Y, Y', Z, Z' have the meanings given above, with the proviso that at least one atom from W, X, Y, Z and at least one atom from W', X', Y', Z' contains, identically or independently of one another, a heteroatom selected from Si, B, N, O, S or P, and furthermore:

$Q^-$ is an anionic counterion, preferably selected from the group consisting of:

$F^-$, $Cl^-$, $Br^-$, $I^-$, $CN^-$, $[ClO_4]^-$, $[BF_4]^-$, $[BF_zR^F_{4-z}]^-$, $[BF_z(CN)_{4-z}]^-$, $[B(CN)_4]^-$, $[B(C_6F_5)_4]^-$, $[B(OR^9)_4]^-$, $[N(CF_3)_2]^-$, $[N(CN)_2]^-$, $[AlCl_4]^-$, $[SbF_6]^-$, $[SiF_6]^-$, $[R^9SO_3]^-$, $[R^FSO_3]^-$, $[(R^FSO_2)_2N]^-$, $[(R^FSO_2)_3C)]^-$, $[(FSO_2)_3C]^-$, $[R^9CH_2OSO_3]^-$, $[R^9C(O)O]^-$, $[R^FC(O)O]^-$, $[CCl_3C(O)O]^-$, $[(CN)_3C]^-$, $[(CN)_2CR^9]^-$, $[(R^9O(O)C)_2CR^9]^-$, $[P(C_nF_{2n+1-m}H_m)_yF_{6-y}]^-$, $[P(C_6F_5)_yF_{6-y}]^-$, $[R^9_2P(O)O]^-$, $[R^9P(O)O_2]^{2-}$, $[(R^9O)_2P(O)O]^-$, $[(R^9O)P(O)O_2]^{2-}$, $[(R^9O)(R^9)P(O)O]^-$, $[R^F_2P(O)O]^-$, $[R^FP(O)O_2]^{2-}$, where the substituents $R^F$ each, independently of one another, denote: perfluorinated and straight-chain or branched alkyl having 1-20 C atoms, perfluorinated and straight-chain or branched alkenyl having 2-20 C atoms and at least one double bond, perfluorinated phenyl and saturated, partially or fully unsaturated cycloalkyl having 3-7 C atoms, which may be substituted by perfluoroalkyl groups, where the substituents $R^F$ in $[R^F_2P(O)O]^-$ may be connected to one another by single or double bonds, so that together they form a three- to eight-membered ring, and where one carbon atom or two non-adjacent carbon atoms of the substituent $R^F$ may be replaced by atoms and/or atom groups selected from the group —O—, —C(O)—, —S—, —S(O)—, —SO$_2$—, —N=, —N=N—, —NR$^1$—, —PR$^1$— and —P(O)R$^1$— or may contain an end group $R^1$—O—SO$_2$— or $R^1$—OC(O)—, where $R^1$ has the meaning given above and where the substituents $R^9$ each, independently of one another, denote: hydrogen, straight-chain or branched alkyl having 1-20 C atoms, straight-chain or branched alkenyl having 2-20 C atoms and at least one double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, and $R^9$ may be partially substituted by $CN^-$, $NO_2^-$, $F^-$, $Cl^-$, $Br^-$ or $I^-$, where the two substituents $R^9$ in the anions $[(R^9)_2P(O)O]^-$, $[(R^9O(O)C)_2CR^9]$ and $[(R^9O)(R^9)P(O)O]^-$ may be connected to one another by single or double bonds, so that together they form a three- to eight-membered ring, and where a carbon atom of $R^9$ may be replaced by atoms and/or atom groups selected from the group —O—, —C(O)—, —C(O)O—, —S—, —S(O)—, —SO$_2$—, —SO$_3$—, —N=, —N=N—, —NH—, —NR$^1$—, —PR$^1$— and —P(O)R$^1$—, —P(O)R$^1$O—, —OP(O)R$^1$O—, —PR$^1_2$=N—, —C(O)NH—, —C(O)NR$^1$—, —SO$_2$NH— or —SO$_2$NR$^1$—, where $R^1$ has the meaning given above and the variables n, m, y and z are each integers, and n denotes 1 to 20,
m denotes 0, 1, 2 or 3,
y denotes 0, 1, 2, 3 or 4,
z denotes 0, 1, 2 or 3, where $Q^-$ may also be any desired mixture of the said anions.

The preferred embodiments of the symbols used correspond here to those as already indicated above for the compounds of the formulae (1) to (3).

It is furthermore essential to the invention that at least one atom from W, X, Y, Z and at least one atom from W', X', Y', Z' contains, identically or independently of one another, a heteroatom selected from Si, B, N, O, S or P. X, X', Z, Z' and Y, Y' are preferably heteroatoms, particularly preferably X, X' and Z, Z'. In a particularly preferred embodiment of the invention, X, X' and Z, Z' are nitrogen.

Particularly preferred anions Q- are $F^-$, $Cl^-$, $Br^-$, $I^-$, $CN^-$, $[ClO_4]^-$, $[BF_4]^-$, $[R^9CH_2OSO_3]^-$, $[SbF_6]^-$ and $[PF_6]^-$, and very particularly preferably $Cl^-$, $Br^-$, $I^-$, $[BF_4]^-$ and $[PF_6]^-$.

If two substituents $R^F$ or $R^9$ in an anion $Q^-$ are connected to one another by single or double bonds, they can form a common three- to eight-membered ring, preferably a five- to seven-membered and particularly preferably a five- or six-membered ring.

A preferred example of a bisimidazolium salt of the formula (4) according to the invention is characterised in that X, X', Z, Z' are equal to nitrogen, Y, Y' are equal to —CH=, W, W' are equal to carbon, A is equal to —CH=CH—, Q is equal to $Cl^-$ or $PF_6^-$ and R, R' are equal to alkyl, preferably methyl, ethyl or n-propyl.

A preferred example of a biscarbene of the formula (5) according to the invention is characterised in that X, X', Z, Z' are equal to nitrogen, Y, Y' are equal to —CH=, W, W' are equal to carbon, A is equal to —CH=CH—, and R, R' are equal to alkyl, in particular methyl, ethyl or n-propyl.

In accordance with the invention, the biscarbene (5) may also be in partially protonated form, resulting in a monocarbene, which is covered by the general formula (5) for the purposes of the present invention and is thus likewise a subject-matter of the invention.

The present application furthermore relates to a process for the preparation of the above-mentioned metal complexes.

This preparation is carried out in accordance with the invention using compounds of the formula (4) or of the formula (5) as biscarbene ligand or as monocarbene ligand. Suitable processes are, in particular, the processes, known to the person skilled in the art, of deprotonation of ligand precursors, preferably in situ, the complexing of free, isolated mono- and biscarbene ligands, the oxidative addition of haloformamidinium derivatives, the cleavage of electron-rich olefins by means of metal compounds and the transmetallation of metal carbene complexes. Suitable preparation processes are disclosed, for example, in F. E. Hahn, M. C. Jahnke, Angew. Chem. 2008, 120, 3166-3216; Angew. Chem. Int. Ed. 2008, 47, 3122-3172 and the literature cited therein.

A particularly suitable process is the deprotonation of corresponding ligand precursors of the formula (4) and subsequent reaction with a metal compound. In addition, isolated representatives of biscarbenes of the formula (5) can also be reacted with metal compounds or also monocarbenes thereof. A further possibility is the reaction of suitable metal complexes of the formulae (1), (2) or (3) with metal compounds (transmetallation) and the deprotonation of (3), if necessary with subsequent reaction with a further metal compound to form metal complexes of the formula (2).

The preparation of the metal complexes (1), (2) and (3) according to the invention is preferably carried out by deprotonation of ligand precursors, preferably in situ, and reaction with suitable metal compounds or, in the case of the metal complexes (1) and (2) according to the invention, the deprotonation of the metal complexes (3) according to the invention and, in the case of the metal complexes (2), the subsequent reaction with suitable metal compounds.

The deprotonation of compounds of the formula (4) is generally carried out by means of basic anions and under the conditions as described below for the preparation of the mono- and biscarbene of the formula (5) starting from compounds of the formula (4).

The metallation of the carbene of the formula (5) thus generated in situ or of the isolated carbene of the formula (5) is carried out using suitable metal compounds to give the desired metal complex of the formula (1), (2) or (3). The metallation is generally carried out by addition of the corresponding metal compound to the reaction mixture obtained by deprotonation or of the isolated carbene, which is dissolved or suspended in a suitable solvent.

The metallation of the carbene previously isolated or generated in situ is carried out in a suitable solvent, preferably in a polar aprotic solvent, for example tetrahydrofuran, acetonitrile or dimethyl sulfoxide, by addition of the corresponding metal complexes. In general, the reaction is carried out at a temperature of −110 to 180° C., preferably at −30 to 100° C., particularly preferably at 0 to 50° C. The reaction duration is generally 1 minute to 5 days, preferably 1 hour to 1 day.

In the case of transmetallation, suitable metal carbene complexes of the formulae (1), (2) and (3) are initially introduced in a suitable solvent, preferably in a polar aprotic solvent, for example tetrahydrofuran, acetonitrile or dimethyl sulfoxide, and metal compounds are added. In general, the reaction is carried out at a temperature of −30 to 200° C., preferably at 20 to 120° C. The reaction duration is generally 1 minute to 5 days, preferably 1 hour to 2 days.

Depending on the reactivity and stoichiometry of the bases and metal salts used, the deprotonation of the bisimidazolium salts of the formula (4) may take place only partially, giving metal complexes of the formula (3) which contain a corresponding monocarbene as ligand instead of the biscarbene of the formula (5)

Suitable metal compounds for the preparation of metal complexes of the formulae (1), (2) and (3) are, for example, $PdCl_2$, $PdCl_2(PPh_3)_2$, $Pd(PPh_3)_4$, $Pd_2(dibenzylideneacetone)_3$, allylpalladium chloride, $[PdCl_2(CH_3CN)_2]$, $Pd(CH_3CN)_4(BF_4)_2$, $NiCl_2$, $NiBr_2(dimethoxyethane)$, bis(1, 5-cyclooctadiene)nickel, $NiCl_2(PPh_3)_2$, $Ru(Cl)_2(PPh_3)_2$(carbene), $CpRuCl(PPh_3)_2$, $[CpRu(CO)_2]_2$, $[CpRu(CH_3CN)_3]^+$, $[Cp*Ru(CH_3CN)_3]^+$, $[RuCl_2(CO)_3]_2$, $RuCl_2(dmso)_4$, di-µ-chlorobis[(p-cymene)chlororuthenium(II)], $[RuCl_2(C_6H_6)]_2$, $RuCl_3$, $RuI_3$, tris(acetylacetonato)ruthenium(III), bis (1,5-cyclooctadiene)rhodium, acetylacetonatobis(ethylene) rhodium, bis-(dicarbonylchlororhodium(I)), $RhCl_3*xH_2O$, acetylacetonatoiridium(I), tris-(acetylacetonato)iridium(III), bis(1,5-cyclooctadiene)iridium, bis(dicarbonyl-chloroiridium(I)), iridium trihalide, optionally in the form of the hydrate, $Na_2[Ir(acac)_2Cl_2]$, $PtCl_2$, $PtCl_2(PPh_3)_2$, $Pt(PPh_3)_4$, bis(1,5-cyclooctadiene)-platinum, hexachloroplatinate(IV), $(DMSO)_2PtMe_2$, $CuCl_2$, $CuCl$, $CuO_2$, $Cu_2O_2$, $CuI_2$, $CuI$ $CuBr_2$, $CuBr$, $Ag_2O$, Ag(tosylate), Ag(triflate), $AgNO_3$, AuCl, $AuCl(PPh_3)$, $AuCl(SMe_2)$, AuCl(tetrahydrothiophene), $AuCl_3$, $TiCl_3$, $TiCl_4$, Ti(O-i-propyl)$_4$, Ti(Nalkyl$_2$)$_4$, $TiCl_2(Nalkyl_2)_2$, $CpTiCl_3$, $Cp_2TiCl_2$, $ZrCl_4$, $Zr(Nalkyl_2)_4$, $ZrCl_2(Nalkyl_2)_2$, $CpZrCl_3$, $Cp_2ZrCl_2$, $W(CO)_6$, $W(CO)_5(THF)$, $W(CO)_5(pyridine)$, $Cr(CO)_6$, $Cr(CO)_5(THF)$, $Cr(CO)_5(pyridine)$, $Mo(CO)_6$, $Mo(CO)_5(THF)$, $Mo(CO)_5(pyridine)$, $CoCl_2$, $Co_2(CO)_8$, $FeCl_2$, $FeCl_3$, $FeBr_2$, $FeBr_3$, $Fe(CO)_5$, $Fe_2(CO)_9$.

Instead of deprotonation by addition of a base, it is also possible to employ suitable metal compounds with a basic anion, for example the diacetates or acetylacetonates of Pd(II) or Ni(II), acetylacetonates of Ir(I), or Rh(I) and Ir(I) compounds which carry alkoxy ligands, and $Cu_2O$ and $Ag_2O$.

Particularly suitable for the metal carbene complexes of the formulae (1), (2) and (3) employed for the transmetallation are the complexes where M, M'=Ag and Cu. The transmetallation is carried out onto the above-mentioned metal compounds.

The metal complexes of the formulae (1), (2) and (3) obtained are worked up by methods known to the person skilled in the art. The work-up can be carried out, for example, by removal of the solvent (by distillation or by filtration) and subsequent chromatography of the resultant product or recrystallisation of the resultant product.

The bisimidazolium salts of the formula (4) are employed in a molar ratio to the basic anions of generally 2:1 to 1:4, preferably 1:2.2 to 1.2:1.

In the preparation of metal complexes of the formulae (1), (2) and (3), the imidazolium salts or mono- and biscarbenes of the formulae (4) and (5), or the metal complexes of the formulae (1), (2) and (3) employed for the transmetallation are employed in a molar ratio to the suitable metal complexes of generally 8:1 to 1.8:1, preferably with a ratio in accordance with the stoichiometry with an excess of the mono- and biscarbene of 0 to 20% or a deficiency of the mono- and biscarbene of 0 to 10%.

In all cases, suitable salts can also be added to the reaction mixture for replacement of the anionic ligand K by another anionic ligand K.

The present invention therefore furthermore relates to a process for the preparation of a compound of the formula (1), (2) or (3) by reaction of a compound of the formula (4) or formula (5) as bis- or monocarbene ligand by deprotonation of ligand precursors or by complexing of mono- or biscarbene ligands or by oxidative addition of haloformamidinium derivatives or by the cleavage of electron-rich olefins by means of metal compounds or by the transmetallation of metal carbene complexes.

The invention furthermore relates to a process for the preparation of the bisimidazolium salts of the formula (4), which are prepared in accordance with the invention by a process which is explained by way of example at this point with reference to a four-step process for the preparation of compound 4:

(i) reaction of 3,6-dimethylpyridazines with a halogenating reagent to give the corresponding di(halomethyl)pyridazines 1.

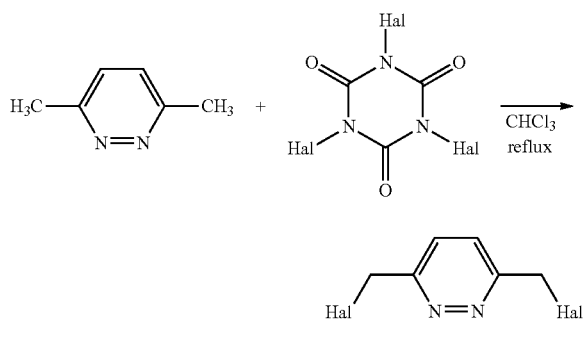

(ii) Reaction of the di(halomethyl)pyridazines with primary amines to give the corresponding aminomethylpyridazines 2.

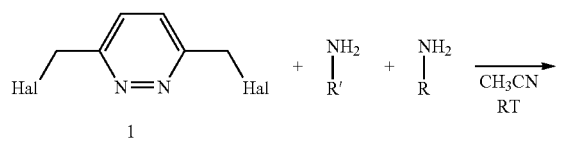

(iii) Formamidation of the corresponding di(aminomethyl) pyridazines using formic acid with promotion by acetic anhydride or other suitable formic acid derivatives to give the di(formamidylmethyl)pyridazines 3.

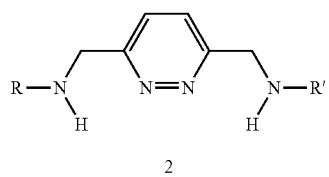

(iv) Cyclisation of the corresponding di(formamidomethyl) pyridazines using phosphoryl chloride or other suitable haloformamide formers to give the bisimidazolium salt 4(Hal) and optionally salt exchange for replacement of the counterion by Q⁻ to give the bisimidazolium salt 4.

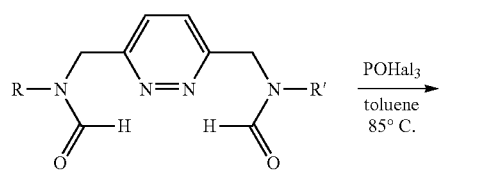

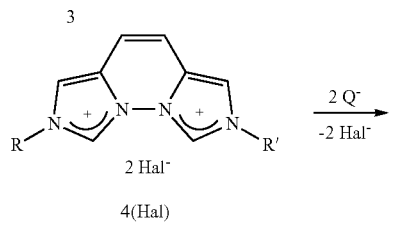

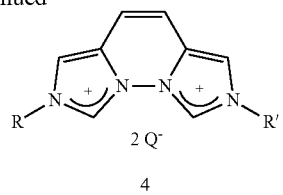

Step (i) is generally carried out in solution. Suitable solvents are halogenated hydrocarbons, such as chloroform, dichloromethane, dichloroethane or carbon tetrachloride; chloroform is preferred.

Typical halogenating agents are trihaloisocycanuric acid or N-halosuccinimide; trichloroisocyanuric acid is preferred.

In step (i), 3,6-dimethylpyridazine is usually initially introduced, and the halogenating agent is added in small portions over a period of 5 minutes to 3 days; 15 minutes to 5 hours are preferred, particularly preferably 30 to 90 minutes.

The reaction solution is generally heated to −10 to 180° C., preferably 25 to 100° C., particularly preferably 35 to 80° C. The reaction mixture is kept at the said temperature over a period of 1 minute to 10 days, preferably 10 minutes to 24 hours, particularly preferably 30 minutes to 3 hours, after addition of the last portion of halogenating reagent. The reaction mixture is subsequently cooled, and the product is worked up by filtration from the by-products or by methods known to the person skilled in the art.

Pyridazine and the halogenation product are generally employed, based on the number of halogen atoms being transferred, in a molar ratio of 1:10 to 1:1, preferably 1:1.5 to 1:3.

The pyridazine compound and derivatives thereof and the halogenating agent employed as starting materials can be prepared by processes known to the person skilled in the art and are in some cases commercially available (R. H. Wiley, J. Macromol. Sci.-Chem. 1987, A24, 1183-1190).

Step (ii) is generally carried out in a solvent. Suitable solvents are alkyl nitriles, ethers or aromatic and aliphatic hydrocarbons, such as toluene or hexane; acetonitrile is preferred.

The reaction is preferably carried out with a primary aliphatic or aromatic amine of the general formula R—NH₂ and R'—NH₂.

Compound 1 and the primary amine are employed in a molar ratio of generally 1:1 to 1:100, preferably 1:2 to 1:50. The amine can be added immediately or in portions. It is also possible to employ two different amines R'—NH₂ and R—NH₂. Two equivalents of the amine here also serve for scavenging of the hydrohalic acids formed. If necessary, other hydrohalic acid scavengers known to the person skilled in the art can also be used.

The reaction solution is warmed at a temperature of generally −30 to 180° C., preferably 0 to 120° C., particularly preferably at 10 to 80° C., for a period of generally 5 minutes to 10 days, preferably 1 hour to 5 days, particularly preferably 5 hours to 2 days.

The reaction mixture is worked up by methods known to the person skilled in the art. Preference is given to extraction of the product with a solvent mixture, preferably consisting of diethyl ether and acetonitrile. The product can be purified further by recrystallisation from a suitable solvent, preferably from diethyl ether.

In the subsequent step (iii), a formamidation is carried out. This can be carried out using formic acid or a derivative, preferably a formic acid in acetic anhydride mixture, which reacts by intermediate formation of a formyl anhydride.

The reaction is preferably carried out in a suitable solvent, preferably in formic acid. The reaction solution is kept at a temperature of generally −30 to 120° C., preferably 0 to 80° C., particularly preferably at 10 to 50° C. The period is generally 1 minute to 5 days, preferably 15 minutes to 12 hours, particularly preferably 30 minutes to 3 hours.

The reaction mixture is worked up by methods known to the person skilled in the art. The mixture is preferably hydrolysed using water and evaporated to dryness in vacuo. The product is extracted by extraction with a suitable solvent, preferably diethyl ether, dried using a suitable desiccant and preferably freed from solvent in vacuo. The product can preferably also be employed in the next step without further purification.

In the subsequent step (iv), cyclisation to the bisimidazolium salt is carried out by processes known to the person skilled in the art. In general, the formamide is activated, preferably by means of acid chloride formers, particularly preferably using phosphoryl chloride, phosphorus trichloride or thionyl chloride.

The reaction is generally carried out in a solvent, preferably in aliphatic or aromatic hydrocarbons, particularly preferably in toluene.

The reaction temperature is generally −30 to 180° C., preferably between 0 to 150° C., particularly preferably between 30 to 120° C.

The product is generally isolated and purified by removal of the solvent in vacuo and washing of the residue with a suitable solvent mixture, for example a THF/pentane mixture.

If necessary, the counterion can be replaced by salt exchange. To this end, the bisimidazolium salt is generally dissolved in water, and the salt of the desired counterion is added. The product is isolated and purified by methods known to the person skilled in the art, particularly by crystallisation.

An alternative process for the preparation of the bisimidazolium salt of the formula (4) can start from 3,6-diformylpyridazine, which can be reacted with primary alkyl- and arylamines by a known process (J. R. Price, Y. Lan, S. Brooker Dalton Trans. 2007, 1807-1820; S. Brooker, R. J. Kelly, P. G. Plieger Chem. Commun. 1998, 1079) and with hydroxylamine (N. K. Szymczeak, L. A. Berben, J. C. Peters, Chem. Commun. 2009, 6729-6731; or B. Mernari, M. Lagranee, J. Heterocyclic Chem. 1996, 33, 2059-2061) to give the respective bisimines a.

Starting from the bisimines a, cyclisation with the aid of silver triflate and chloromethyl pivalate can lead directly to the bisimidazolium salt 4 of the general formula (4), as has been described by Glorius for bisimines, but also for the preparation of imidazo[1,5-a]pyridinium salts (F. Glorius US 2005/0240025 A1; C. Burstein, C. W. Lehmann, F. Glorius, Tetrahedron 2005, 61, 6207-6217).

A further possibility is reduction of the bisimines using sodium borohydride to give the corresponding bis(aminomethyl)pyridazine, as is known, for example, from the literature (P. R. Plieger, A. J. Downard, B. Moubaraki, K. S. Murray, S. Brooker, Dalton Trans. 2004, 2157-2165; S. Brooker, S. S. Iremonger, P. G. Plieger, Polyhedron 2003, 22, 665-671). This can then, after steps (iii) and (iv), likewise be converted into the bisimidazolium salt 4 corresponding to the general formula (4).

In the case of hydroxylamine, reduction using sodium borohydride or catalytic hydrogenation to give 3,6-di(aminomethyl)pyridazine d is possible, this can then be formylamidated using formic acid to give compound c (analogously to step (iii)) and cyclised using phosphoryl chloride or an analogous reagent to give di(imidazo)pyridazine f analogously to step (iv). This can then be reacted with alkyl halides or electron-deficient aryl halides to give the bisimidazolium salts 4 corresponding to the formula (1). This route is analogous to that described for imidazo[1,5-a]pyridinium salts (M. Nonnenmacher, dissertation, Heidelberg, 2008).

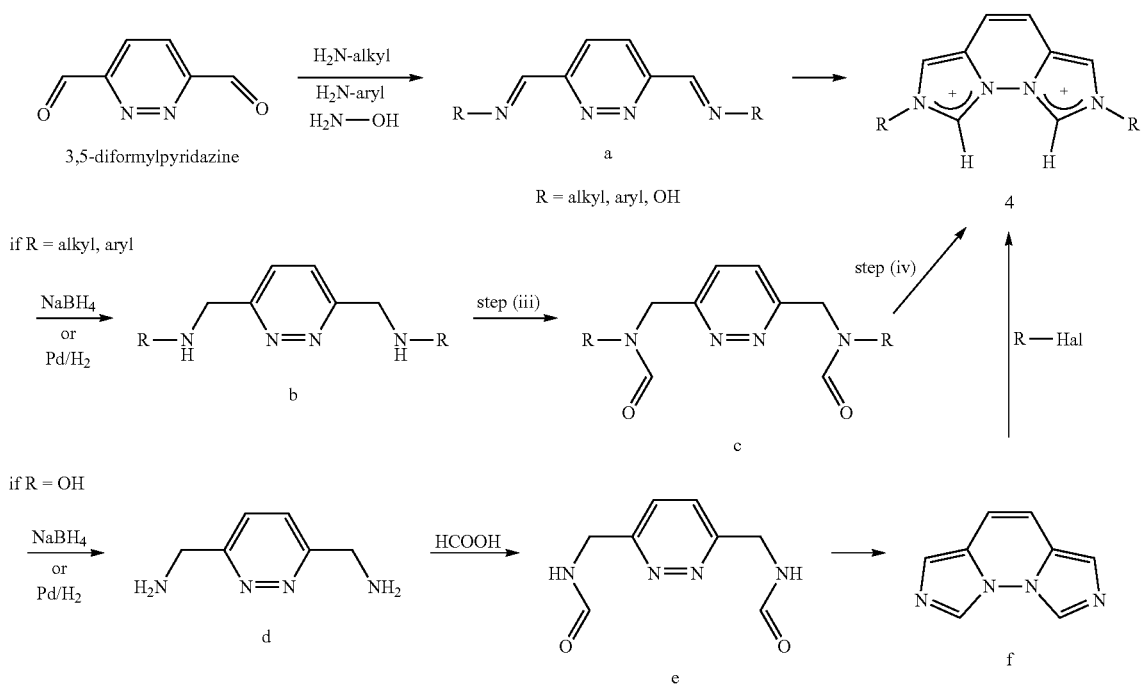

The present application furthermore relates to the use of compounds of the formula (4) as ionic liquid.

The present application furthermore relates to a process for the preparation of the biscarbene of the general formula (5).

The preparation is carried out in accordance with the invention starting from bisimidazolium salts of the general formula (4) by deprotonation, for example by processes known to the person skilled in the art. These also include the incomplete deprotonation of (4), resulting in a monocarbene or a mixture of bisimidazolium salt (4) and monocarbene, bisimidazolium salt and biscarbene (5), or monocarbene and biscarbene (5), which can be controlled by the base equivalents.

The deprotonation is generally carried out in a solvent. Suitable solvents are cyclic and acyclic ethers, aliphatic and aromatic hydrocarbons, particularly tetrahydrofuran.

Suitable deprotonation reagents are generally medium-strength and strong bases, particularly metal hydrides, metal amides, alkylmetal and arylmetal compounds, metal alkoxides, metal carboxylates and bulky tertiary amines, in particular methyllithium, potassium tert-butoxide, potassium acetate and lithium diisopropylamide.

The deprotonation is carried out using up to 20 equivalents of base per bisimidazolium salt of the formula (4), preferably up to 10 equivalents, particularly preferably up to 1.8 to 2.2 equivalents, in the case of monocarbenes 0.8 to 1.2 equivalents per bisimidazolium salt (I).

The reaction is generally carried out at temperatures of −110 to 100° C., particularly between −78 to 50° C., in particular between −30 to 30° C.

The bisimidazolium salt is usually dissolved or suspended in the solvent, and the base is added in one portion or in portions. When the addition of the base is complete, the reaction mixture is left at the temperature indicated for a further 1 second to 5 days hours, particularly 2 minutes to 6 hours, in particular 5 minutes and 2 hours. The mono- or biscarbene can be processed further in situ or separated off from the by-products by filtration and isolated subsequent evaporation of the filtrate to dryness in vacuo, during which the temperature must be matched to the stability of the carbene. The mono- and biscarbene of the formula (5) can be recrystallised by a suitable solvent.

The present invention furthermore relates to the use of compounds of the formula (5) as organocatalyst, which is also taken to mean the monocarbenes generated by incomplete deprotonation of the bisimdazolium salts (4) or by incomplete protonation.

The invention furthermore relates to the use of the metal complexes of the formulae (1), (2) and (3) in a process selected from the group consisting of carbonylation, hydroamination, hydrogenation, hydroaminomethylation, hydroformylation, hydrosilylation, hydrocyanation, hydrodimerisation, oxidation, oxidative coupling, Heck reaction, Tsuji-Trost coupling, Suzuki-Miyaura coupling, Kumada coupling, Negishi coupling, Stille coupling, Sonogashira reaction, $C(sp^3)$-$C(sp^3)$ coupling reactions, $C(sp^3)$-$C(sp^2)$ coupling reactions, Hartwig-Buchwald amination, Ullmann-Goldberg coupling, isomerisation, rearrangement, Diels-Alder reaction, metathesis, C—H activation of alkanes and alkenes, 1,4-functionalisation of 1,3-dienes, telomerisation, oligomerisation and/or polymerisation. They are generally employed as catalysts in the said reactions.

The complexes of the formula (1), (2) or (3) described above or the preferred embodiments indicated above can furthermore also be used as active component in an electronic device. The present invention therefore furthermore relates to the use of a compound of the formula (1), (2) or (3) or the preferred embodiments indicated above in an electronic device.

The present invention again furthermore relates to an electronic device comprising at least one compound of the formula (1), (2) or (3) or the preferred embodiments indicated above. The electronic device according to the invention comprises anode, cathode and at least one layer which comprises at least one compound of the above-mentioned formula (1), (2) or (3). Preferred electronic devices here are selected from the group consisting of organic electroluminescent devices (OLEDs), organic integrated circuits (O—ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs), light-emitting electrochemical cells (LECs) or organic laser diodes (O-lasers), comprising in at least one layer at least one compound of the above-mentioned formula (1), (2) or (3) or the preferred embodiments indicated above.

Particular preference is given to organic electroluminescent devices. The active component is generally the organic or inorganic materials introduced between anode and cathode, for example charge-injection, charge-transport or charge-blocking materials, but in particular emission materials and matrix materials. The compounds according to the invention exhibit particularly good properties as emission material in organic electroluminescent devices. A preferred embodiment of the invention is therefore organic electroluminescent devices.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Inter-layers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one or more emitting layer. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1), (2) or (3) or the preferred embodiments indicated above as emitting compound in one or more emitting layers.

If the compound of the formula (1), (2) or (3) or the preferred embodiments indicated above is employed as emitting compound in an emitting layer, it is preferably employed in combination with one or more matrix materials. A matrix material in the sense of the present invention is a material which can be used in an emission layer in order to dope in the emitting material therein in typically a volume concentration of <25%, but does not itself contribute significantly to light emission, in contrast to the doped-in emitter material. Which materials contribute significantly to light emission in an emitter layer and which do not, and which materials are thus to be regarded as emitters and which are to be regarded as matrix materials can be recognised by comparison of the electroluminescence spectrum of the OLED in which the emitter layer is present with photoluminescence spectra of the individual materials. The mixture of the compound of the formula (1), (2) or (3) or the preferred embodiments indicated above and the matrix material comprises between 0.1 and 99% by vol., preferably between 1 and 90% by vol., particularly preferably between 3 and 40% by vol., in particular between 5 and 15% by vol., of the compound of the formula (1), (2) or (3) or the preferred embodiments indicated above, based on the entire mixture of emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the entire mixture of emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP(N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107, WO 2011/088877, WO 2011/116865, WO 2011/137951 or the unpublished application EP 11003232.3.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not or not significantly involved in charge transport, as described, for example, in WO 2010/108579.

It is furthermore preferred to employ a mixture of two or more triplet emitters together with a matrix. The triplet emitter having the shorter-wave emission spectrum serves as co-matrix here for the triplet emitter having the longer-wave emission spectrum. Thus, for example, the complexes of the formula (1), (2) or (3) according to the invention can be employed as co-matrix for triplet emitters emitting at longer wavelength, for example for green- or red-emitting triplet emitters. Likewise, the complexes according to the invention can be employed as triplet emitters together with a metal complex emitting at shorter wavelength. Preference is given here to the combination of two platinum complexes or the combination of one platinum complex with one iridium complex.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

In the further layers, it is generally possible to use all materials as are used in accordance with the prior art for the layers, and the person skilled in the art will be able to combine each of these materials in an electronic device with the materials according to the invention without inventive step.

The device is structured correspondingly (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1), (2) or (3) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1), (2) or (3) or the preferred embodiments indicated above.

The electronic devices according to the invention, in particular organic electroluminescent devices, are distinguished by the following surprising advantages over the prior art:
1. Organic electroluminescent devices comprising compounds of the formula (1), (2) or (3) as emitting materials have a good lifetime.
2. Organic electroluminescent devices comprising compounds of the formula (1), (2) or (3) as emitting materials simultaneously have good efficiency.

These above-mentioned advantages are not accompanied by an impairment of the other electronic properties.

The invention is explained in greater detail by the following examples, without wishing to restrict it thereby. The person skilled in the art will be able to produce further electronic devices according to the invention from the descriptions without inventive step and thus carry out the invention throughout the range claimed.

EXAMPLES

The reactions were carried out, unless stated otherwise, with exclusion of air and moisture using the Schlenk technique. The inert gas used was argon 5.0 from Westphalen AG. The glass equipment used was dried before use by heating with a hot-air gun in an oil-pump vacuum ($<10^{-3}$ mbar) and aerated with argon. The solvents were rendered absolute either by standard methods (W. L. F. Armarego, C. L. L. Chai, "Purification of Laboratory Chemicals", 5th Edn., Elsevier, Oxford 2003) or using the MBraun-SPS-800 Solvent Purification System from MBraun. Deuterated solvents were likewise dried by standard methods, distilled and subsequently degassed by freezing in liquid nitrogen, evacuation of the gas space located above and saturation with argon. The solvent transfer was carried out by means of the septum and cannula technique. Solids were separated off using filter syringes (Minisart SRP 15 0.45 μm from Sartorius), glass suction filters having the D4 pore size or using Whatman® filters (glass microfibre filters) which have been attached to Teflon cannulas using Teflon tape. Air- and moisture-sensitive solids and liquids were handled in a glove box (MBraun Labmaster) from MBraun with argon 5.0 as inert gas. The standard NMR tubes and the Young® NMR tubes with Teflon screw cap which can be sealed in an air-tight manner are obtained from Deutero. Commercially available chemicals were purchased from Acros and Sigma-Aldrich.

The nuclear resonance spectra were recorded on a Bruker AVII+400 spectrometer with BACS-60 sample changer. The $^{13}$C-NMR spectra were recorded with broadband $\{^{1}H\}$ decoupling. The chemical shifts (δ) are indicated in ppm relative to tetramethylsilane. The coupling constants (J) are shown in hertz (Hz). The standardisation in $^{1}$H-NMR spectra (400.13 MHz) is carried out internally by calibration of the residual proton signals of the deuterated solvents: THF-$d_7$ δ=1.73, 3.58; CD$_2$HCN δ=1.94; DMSO-$d_5$ δ=2.50 and CHCl$_3$ δ=7.27. The internal standard used for the $^{13}$C$\{^{1}H\}$-NMR spectra (100.61 MHz) are the solvent signals: THF-$d_8$ δ=25.5, 67.7; CD$_3$CN δ=1.4, 118.7; CDCl$_3$ δ=77.0 and DMSO-$d_6$ δ=39.5. In the description of the spectra, the following abbreviations are used for the multiplicity of the signals: s=singlet, d=doublet, t=triplet, q=quartet, m=multiplet, sext=sextet. The addition br denotes a broad signal. The signals were assigned by suitable 2D experiments.

The mass spectra were measured on a Bruker Daltonics APEX II FT-ICR in acetonitrile or methanol as solvent. All measurements were carried out in the Mass Spectrometry Department at the University of Tübingen.

The elemental analyses were carried out in the Department of Inorganic Chemistry at the University of Tübingen on a varioMicro Cube and a varioEL-II from Elementar.

Example 1: 3,6-Bis(chloromethyl)pyridazine

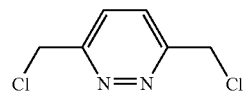

A solution of 3,6-dimethylpyridazine (6.60 g, 61.0 mmol) in absolute CHCl$_3$ (400 ml) is heated to the boil under a protective-gas atmosphere. Trichloroisocyanuric acid (12.3 g, 52.9 mmol) is then added in small portions over the course of one hour. The mixture foams briefly in each case, and a brownish suspension forms, which is heated under reflux for a further 2.5 h. After cooling to room temperature, the beige solid is separated off via a frit (D4), and the filtrate is washed twice with 150 ml of a 0.2 M aqueous NaOH solution each time and twice with 200 ml of water each time. The organic phase is dried over Na$_2$SO$_4$, and the solvent is removed in vacuo, leaving a brown oil, to which a little pentane is added, and the mixture is stored overnight at −30° C. The brown crystals formed are filtered off and extracted with 50 ml of abs. diethyl ether. The ether-insoluble brown solid is discarded, and the ether solution is evaporated to dryness in vacuo. The product is obtained as a beige solid (4.49 g, 42%). In order to prevent decomposition, the product is stored at −30° C. under protective gas.

$^{1}$H-NMR (CDCl$_3$, 400.13 MHz):
δ=7.77 (s, 2H, 4/5-H), 4.92 (s, 4H, CH$_2$).
$^{13}$C$\{^{1}H\}$-NMR (CDCl$_3$, 100.61 MHz):
δ=158.9 (C3/6), 127.2 (C4/5), 44.2 (CH$_2$).
Elemental Analysis:
calculated: C, 40.71. H, 3.42. N, 15.82.
found: C, 40.26. H, 3.04. N, 15.62.

Example 2:
3,6-Bis(n-propylaminomethyl)pyridazine

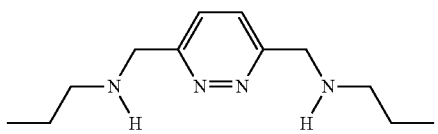

n-Propylamine (1.85 ml, 1.33 g, 22.6 mmol) is added to a solution of 3,6-bis(chloromethyl)pyridazine from Ex. 1 (200 mg, 1.13 mmol) in absolute acetonitrile (5 ml) under protective gas. The brownish solution is stirred overnight at room temperature and then evaporated to dryness. The residue is extracted twice with 5 ml of a mixture of diethyl ether and acetonitrile (1:1) each time and once with diethyl ether (5 ml). The solution is evaporated in vacuo, and the oily residue is recrystallised from diethyl ether at −30° C. The product is obtained as a yellow-brown solid (174 mg, 69%).

$^1$H-NMR (CD$_3$CN, 400.13 MHz):

δ=7.56 (s, 2H, 4/5-H), 3.99 (s, 4H, NCH$_2$), 2.54 (t, $^3J_{HH}$=7.1 Hz, 4H, NCH$_2$—Pr), 1.91 (s, br, 2H, NH), 1.48 (sext, $^3J_{HH}$=7.3 Hz, 4H, CH$_2$—Pr), 0.90 (t, $^3J_{HH}$=7.4 Hz, 6H, CH$_3$—Pr).

$^{13}$C{$^1$H}-NMR (CD$_3$CN, 100.61 MHz):

δ=162.7 (C3/6), 127.5 (C4/5), 54.3 (NCH$_2$), 52.4 (NCH$_2$—Pr), 24.3 (CH$_2$—Pr), 12.5 (CH$_3$—Pr).

The following compounds are prepared analogously:

Example 9:
3,6-Bis(n-propylformamidomethyl)pyridazine

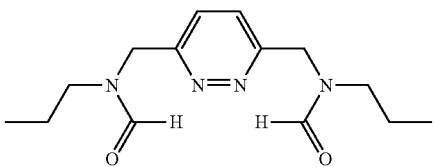 [SMILES: CCCN(C=O)Cc1ccc(CN(C=O)CCC)nn1]

3,6-Bis(n-propylaminomethyl)pyridazine from Ex. 2 (1.60 g, 7.18 mmol) is added to a mixture of formic acid (purity 99+%, 10 ml) and acetic anhydride (1.5 ml) under an argon atmosphere. Slight evolution of gas occurs, and a yellow-brown solution forms, which is stirred at room

| Ex. | Amine | Product | Yield |
|---|---|---|---|
| 3 | —NH$_2$ 10 ml, 2M solution in THF | | 63% |
| 4 | H$_2$N-C(CH$_3$)$_3$ | | 40% |
| 5 | neopentylamine | | 65% |
| 6 | 2,4,6-trimethylaniline, stir overnight at 50° C. | | 35% |
| 7 | phenethylamine | | 60% |
| 8 | neopentylamine + 1,4-bis(chloromethyl)phthalazine | | 55% | temperature for 1.5 h. 5 ml of water are then added, and the solution is evaporated to dryness in vacuo. The oily brown residue is extracted five times with 10 ml of diethyl ether each time. The ethereal solution is evaporated to dryness in vacuo after drying over $Na_2SO_4$, and the product is obtained as a yellowish oil in the form of its three isomers A, B and C, which can be employed without further purification (1.75 g, 88%).

$^1$H-NMR ($CD_3CN$, 400.13 MHz):

(isomers A, B and C were assigned as far as possible)

δ=8.34, 8.33, (each s, 3H, CHO, A and B), 8.21, 8.20 (each s, 3H, CHO, B and C), 7.72 (s, 2H, 4/5-H, A), 7.65 (d, 1H, $^3J_{HH}$=8.6 Hz, 4/5-H, B), 7.56 (d, 1H, $^3J_{HH}$=8.6 Hz, 4/5-H, B), 7.51 (s, 2H, 4/5-H, C), 4.75 (s, 4H, $NCH_2$, A), 4.73 (s, 2H, $NCH_2$, B), 4.70 (s, 2H, $NCH_2$, B), 4.69 (s, 4H, $NCH_2$, C), 3.24-3.28 (m, 6H, $NCH_2$—Pr, B and C), 3.06-3.10 (m, 6H, $NCH_2$—Pr, A and B), 1.42-1.51 (m, 6H, $CH_2$—Pr, B and C), 1.30-1.40 (m, 6H, $CH_2$—Pr, A and B), 0.71-0.78 (m, 18H, $CH_3$—Pr, A, B and C).

$^{13}$C{$^1$H}-NMR ($CD_3CN$, 100.61 MHz):

(isomers A, B and C were assigned as far as possible)

δ=163.5, 163.3 (in each case 2 signals, CHO, A, B and C), 158.8, 158.4 (in each case 2 signals, C3/6, A, B and C), 126.7 (C4/5, A), 126.6 (C4/5, B), 126.5 (C4/5, B), 126.4 (C4/5, C), 50.1 (2 signals, $NCH_2$, A and B), 48.8 (2 signals, $NCH_2$—Pr, B and C), 45.3, 45.2 ($NCH_2$, B and C), 43.4 (2 signals, $NCH_2$—Pr, A and B), 21.1 ($CH_2$—Pr, B and C) 19.8 ($CH_2$—Pr, A and B), 11.0, 10.6 ($CH_3$—Pr, A, B and C).

The following compounds are prepared analogously:

| Ex. | Starting material | Product | Yield |
|---|---|---|---|
| 10 | | | 68% |
| 11 | | | 45% |
| 12 | | | 70% |
| 13 | | | 40% |
| 14 | !! EMBED ISISServer | | 65% |
| 15 | | | 50% |

Example 16: Bisimidazolium Salts

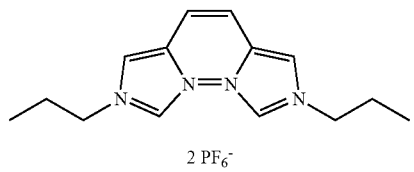

2 PF$_6^-$

POCl$_3$ (1.26 ml, 2.12 g, 14 mmol) is added to a mixture of the three isomers of 3,6-bis(n-propylformamidomethyl)pyridazine from Ex. 9 (1.75 g, 6.28 mmol) in 100 ml of absolute toluene. The reaction mixture is stirred overnight at 85° C., during which a brown oil forms on the flask wall. After 20 h, the solvent is removed in vacuo, and the oily residue is purified using 25 ml of THF, 50 ml of a mixture of THF/pentane (1:1) and 25 ml of pentane. The brownish residue is dissolved in the smallest possible amount of water (about 10 ml). A saturated solution of KPF$_6$ (2.13 g, 13 mmol) in water is added to the aqueous solution, with a beige solid immediately precipitating. The solid is filtered off and washed with cold water (20 ml) and dry diethyl ether (50 ml). Drying in vacuo gives the product as a beige solid (1.82 g, 54%).

$^1$H-NMR (CD$_3$CN, 400.13 MHz):
δ=9.36 (s, 2H, 5/8-H), 8.06 (s, 2H, 3/10-H), 7.57 (s, 2H, 1/2-H), 4.47 (t, $^3J_{HH}$=7.1 Hz, 4H, NCH$_2$), 2.02 (sext, 4H, $^3J_{HH}$=7.3 Hz, CH$_2$), 1.00 (t, 6H, $^3J_{HH}$=7.4 Hz, CH$_3$).

$^{13}$C{$^1$H}-NMR (CD$_3$CN, 100.61 MHz):
δ=127.2 (C5/8), 125.9 (C2a/10a), 119.4 (C3/10), 116.1 (C1/2), 54.8 (NCH$_2$), 24.2 (CH$_2$), 10.7 (CH$_3$).

$^{19}$F-NMR (CD$_3$CN, 376.50 MHz):
δ=−72.9 (d, J$_{FP}$=706.9 Hz, PF$_6^-$).

| Ex. | Starting material | Product | Yield |
|---|---|---|---|
| 17 | *(structure)* | *(structure)* 2 PF$_6^-$ | 49% |
| 18 | *(structure)* | *(structure)* 2 PF$_6^-$ | 30% |
| 19 | *(structure)* | *(structure)* 2 PF$_6^-$ | 43% |
| 20 | *(structure)* | *(structure)* 2 PF$_6^-$ | 25% |
| 21 | *(structure)* | *(structure)* 2 PF$_6^-$ | 48% |

| Ex. | Starting material | Product | Yield |
|---|---|---|---|
| 22 | | | 34% |

-continued

Example 23: Synthesis of the Free Carbene in the NMR Experiment

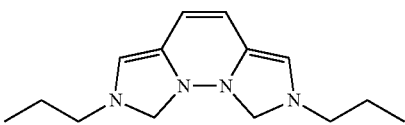 [SMILES: CCCN1C=C2C=CC3=CN(CCC)CN3N2C1]

The bisimidazolium salt from Ex. 6 (10.0 mg, 0.019 mmol) is suspended in 0.5 ml of absolute THF-$d_8$ under an argon atmosphere in a Young NMR tube, and methyllithium (0.8 mg, 0.04 mmol) is added. A brownish solution of the carbene forms, which becomes a dark colour and then black at room temperature with gradual decomposition of the carbene. The $^1$H-NMR spectrum recorded immediately after addition of methyllithium shows the disappearance of the signal for the two imidazolium protons.

$^1$H-NMR (THF-$d_8$, 400.13 MHz):

δ=7.57 (s, 2H, 1/2-H), 7.03 (s, 2H, 3/10-H), 4.19 (t, 4H, $^3J_{HH}$=7.0 Hz, NCH$_2$), 1.93 (sext, 4H, $^3J_{HH}$=7.2 Hz, CH$_2$), 0.95 (t, 6H, $^3J_{HH}$=7.4 Hz, CH$_3$).

$^{13}$C{$^1$H}-NMR (THF-$d_8$, 100.61 MHz):

δ=124.7 (C2a/10a), 117.0 (C3/10), 113.2 (C1/2), 54.7 (NCH$_2$), 22.3 (CH$_2$), 11.4 (CH$_3$), C5/8 is not detected.

Example 24: Pt Carbene Complexes

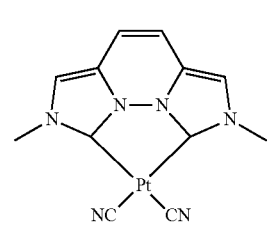

A mixture of 4.80 g (10.0 mmol) of bisimidazolium salt from Ex. 17, 2.47 g (10.0 mmol) of platinum(II) cyanide, 2.97 g (30.0 mmol) of potassium acetate and 100 ml of acetonitrile is stirred at 50° C. for 20 h. After cooling, the reaction mixture is evaporated to about 30 ml, the solid formed is filtered off with suction, washed three times with 5 ml of acetonitrile each time and three times with 5 ml of n-heptane each time and then dried in vacuo. The purification is carried out by fractional sublimation three times (p about 10$^{-6}$ mbar, T=260-280° C.). Yield: 1.27 g (2.9 mmol), 29%. Purity: >99.5% according to $^1$H-NMR.

The following compounds are prepared analogously:

| Ex. | Starting material | Product | Yield |
|---|---|---|---|
| 25 | | | 23% |
| 26 | | | 19% |

| Ex. | Starting material | Product | Yield |
|---|---|---|---|
| 27 | (structure, 2 PF6⁻) | (structure) | 28% |
| 28 | (structure, 2 PF6⁻) | (structure) | 24% |

Example 29: Pt Carbene Complexes

A mixture of 6.32 g (10 mmol) of bisimidazolium salt according to Ex. 21, 3.50 g (10 mmol) of dimethyldi(1-S-dimethylsulfoxidyl)platinum(II), 2.97 g (30 mmol) of potassium acetate and 100 ml of benzonitrile is stirred at 50° C. for 10 h. The reaction mixture is subsequently heated at 160° C. for 12 h, then allowed to cool, the benzonitrile is removed in vacuo, and the residue is chromatographed on silica gel with dichloromethane. The yellow eluate is freed from dichloromethane in vacuo, the residue is chromatographed again on silica gel with dichloromethane and, after the solvent has been stripped off, recrystallised three times from DMF. The further purification is carried out by fractional sublimation three times (p about $10^{-6}$ mbar, T=290-300° C.). Yield: 1.44 g (2.70 mmol), 27%. Purity: >99.5% according to $^1$H-NMR.

Example 30: Ir Carbene Complexes

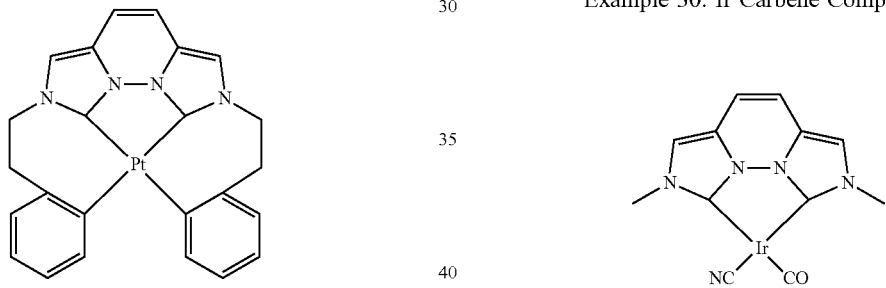

A mixture of 4.80 g (10 mmol) of bisimidazolium salt from Ex. 17, 7.71 g (10 mmol) of carbonylbis(triphenylphosphino)iridium(I) cyanide, 2.97 g (30 mmol) of potassium acetate and 100 ml of acetonitrile is stirred at 50° C. for 20 h. After cooling, the reaction mixture is evaporated to about 30 ml, the solid formed is filtered off with suction, washed three times with 5 ml of acetonitrile each time and three times with 5 ml of n-heptane each time and then dried in vacuo. The purification is carried out by fractional sublimation three times (p about $10^{-6}$ mbar, T=260-280° C.). Yield: 1.21 g (2.59 mmol), 26%. Purity: >99.5% according to $^1$H-NMR.

The following compounds are prepared analogously:

| Ex. | Starting material | Product | Yield |
|---|---|---|---|
| 31 | (structure, 2 PF6⁻) | (structure) | 18% |

| Ex. | Starting material | Product | Yield |
|---|---|---|---|
| 32 | (structure, 2 PF$_6^-$) | (structure) | 22% |

Example 33: Os Carbene Complexes

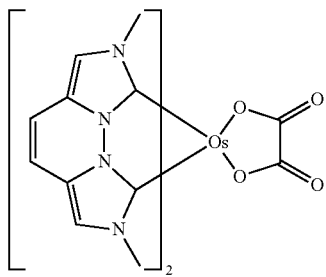

A mixture of 9.6 g (20 mmol) of bisimidazolium salt according to Ex. 17, 4.39 g (10 mmol) of ammonium hexachloroosmate(II), 9.97 g (60 mmol) of dipotassium oxalate and 100 ml of ethylene glycol is stirred at 160° C. for 12 h. After cooling, a solution of 2.26 g (11 mmol) of sodium dithionite in 5 ml of water is added, the mixture is stirred at room temperature for a further 2 h, 300 ml of water are added dropwise, the precipitated solid is filtered off with suction, washed three times with 10 ml of a methanol/water mixture (1:1, vv) each time, three times with 10 ml of methanol each time and then dried in vacuo. The residue is chromatographed on silica gel with dichloromethane. The yellow eluate is freed from dichloromethane in vacuo, the residue is chromatographed again on silica gel with dichloromethane and, after the solvent has been stripped off, recrystallised three times from DMF. The further purification is carried out by fractional sublimation three times (p about $10^{-6}$ mbar, T=340-350° C.). Yield: 2.00 g (3.05 mmol), 30%. Purity: >99.5% according to $^1$H-NMR.

Example 34: Cu Carbene Complex

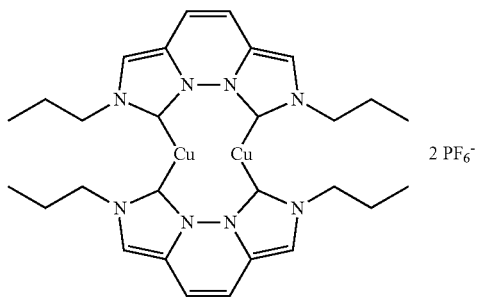

Cu$_2$O (29.5 mg, 0.206 mmol) is added to a solution of the bisimidazolium salt from Ex. 16 (100 mg, 187 µmol) in abs. CH$_3$CN (10 ml). The suspension is stirred overnight at 100° C. After cooling to room temperature, the mixture is filtered through Celite, and the filtrate is evaporated to dryness in vacuo. The residue is extracted with CH$_2$Cl$_2$ (10 ml), and the solution is evaporated to dryness in vacuo. The oily residue is stirred in pentane (10 ml) for 1 h and filtered off. Drying in vacuo gives the product as a beige solid (69 mg, 82%).

$^1$H-NMR (CD$_3$CN, 400.13 MHz):

δ=7.56 (s, 4H, 3/10-H), 7.06 (s, 4H, 2/10-H), 4.42 (t, 8H, $^3J_{HH}$=7.5 Hz, NCH$_2$), 1.99 (sext, 8H, $^3J_{HH}$=7.5 Hz, CH$_2$), 0.98 (t, 12H, $^3J_{HH}$=7.4 Hz, CH$_3$).

$^{13}$C{$^1$H}-NMR (CD$_3$CN, 100.61 MHz):

δ=167.9 (C5/8, from $^1$H, $^{13}$C-HMBC), 126.8 (C2a/10a), 117.7 (C3/10), 113.8 (C1/2), 55.3 (NCH$_2$), 25.6 (CH$_2$), 11.3 (CH$_3$).

Example 35: Ag Carbene Complex

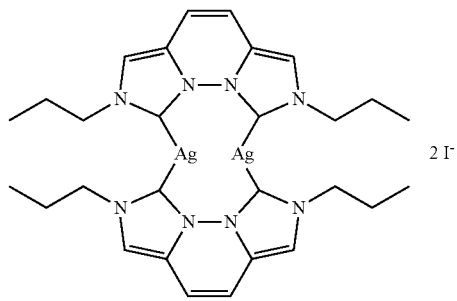

Ag$_2$O (43 mg, 0.206 mmol) is added to a solution of the bisimidazolium salt from Ex. 16 (100 mg, 187 µmol) in abs. CH$_3$CN (10 ml). The dark suspension is stirred overnight at 50° C. with exclusion of light, and sodium iodide (75 mg, 500 mmol) is then added. After cooling to room temperature, the mixture is filtered through Celite, and the solution is evaporated to dryness in vacuo. The residue is extracted with abs. CH$_2$Cl$_2$ (10 ml), and the solution is evaporated to dryness in vacuo. The oily residue is stirred overnight in abs. pentane (10 ml), filtered off and dried in vacuo. The product is obtained as a beige solid (82 mg, 88%).

$^1$H-NMR (DMSO-d$_6$, 400.13 MHz):

δ=8.23 (s, 4H, 3/10-H), 7.40 (s, 4H, 1/2-H), 4.44 (t, 8H, $^3J_{HH}$=7.3 Hz, NCH$_2$), 1.96 (sext, 8H, $^3J_{HH}$=7.4 Hz, CH$_2$), 0.94 (t, 12H, $^3J_{HH}$=7.4 Hz, CH$_3$).

$^{13}$C{$^1$H}-NMR (DMSO-d$_6$, 100.61 MHz):

δ=168.0 (C5/8, $^1$H, $^{13}$C-HMBC), 126.3 (C2a/10a), 117.9 (C3/10), 113.2 (C1/2), 55.3 (NCH$_2$), 24.6 (CH$_2$), 10.7 (CH$_3$).

Elemental analysis: C$_{14}$H$_{18}$AgIN$_4$ calculated: C, 35.24; H, 3.80; N, 11.74.

found: C, 34.64; H, 4.92; N, 11.47.

Example 36: Au Carbene Complex

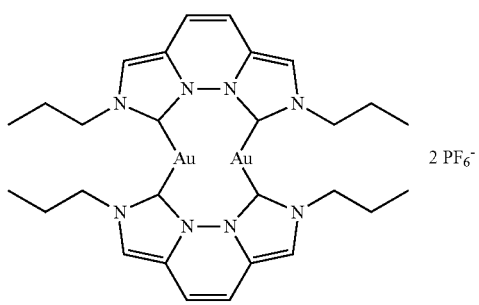

Ag$_2$O (47.7 mg, 206 μmol) is added to a solution of the bisimidazolium salt, Ex. 16 (100 mg, 187 μmol) in abs. CH$_3$CN (10 ml). The dark suspension is stirred overnight at 50° C. with exclusion of light. The precipitate is then filtered off, and [AuCl(SMe$_2$)] (52.4 mg, 178 μmol) is added to the filtrate. A pale solid immediately precipitates out, which becomes a grey colour with time. The mixture is stirred at room temperature for 7 h. The mixture is then filtered through Celite, and the filtrate is evaporated to dryness in vacuo. The yellow residue is extracted with CH$_2$Cl$_2$ (10 ml), the solution is evaporated to dryness, and the oily residue is stirred overnight in pentane (10 ml) with formation of a yellow suspension. Filtration and drying of the solid in vacuo gives the product as a yellow solid (97 mg, 89%).

$^1$H-NMR (CD$_3$CN, 400.13 MHz):

δ=7.80 (s, 2H, 3/10-H), 7.26 (s, 2H, 1/2-H), 4.47 (t, 4H, $^3J_{HH}$=7.3 Hz, NCH$_2$), 2.03 (sext, 4H, $^3J_{HH}$=7.4 Hz, CH$_2$), 0.97 (t, 6H, $^3J_{HH}$=7.4 Hz, CH$_3$).

$^1$H-NMR (DMSO-d$_6$, 400.13 MHz):

δ=8.29 (s, 4H, 3/10-H), 7.44 (s, 4H, 1/2-H), 4.50 (t, 8H, $^3J_{HH}$=7.2 Hz, NCH$_2$), 1.98 (sext, 8H, $^3J_{HH}$=7.4 Hz, CH$_2$), 0.94 (t, 12H, $^3J_{HH}$=7.4 Hz, CH$_3$).

$^{13}$C{$^1$H}-NMR (DMSO-d$_6$, 100.61 MHz):

δ=170.0 (C5/8), 127.2 (C2a/10a), 118.1 (C3/10), 113.8 (C1/2), 55.4 (NCH$_2$), 24.4 (CH$_2$), 10.7 (CH$_3$).

Example 37: Pd Carbene Complex

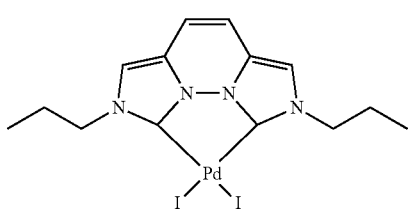

The bisimidazolium salt from Ex. 16 (150 mg, 0.281 mmol) and Pd(OAc)$_2$ (63.0 mg, 0.28 mmol) are dissolved in 15 ml of absolute CH$_3$CN, and NaI (84.2 mg, 0.56 mmol) is added. The yellow solution becomes a dark colour in the process. The mixture is stirred overnight at 50° C., and after 20 h a red solid in yellow solution has formed. The solution is filtered off, and the solid is washed with CH$_3$CN (10 ml) and pentane (5 ml). Drying in vacuo gives the product a red solid.

$^1$H-NMR (DMSO-d$_6$, 400.13 MHz):

δ=8.11 (s, 2H, 3/10-H), 7.16 (s, 2H, 1/2-H), 4.91 (t, 4H, $^3J_{HH}$=7.5 Hz, NCH$_2$), 2.11 (sext, 4H, $^3J_{HH}$=7.3 Hz, CH$_2$), 0.97 (t, 6H, $^3J_{HH}$=7.3 Hz, CH$_3$).

$^{13}$C{$^1$H}-NMR (DMSO-d$_6$, 100.61 MHz):

δ=127.6 (C2a/10a), 118.25 (C3/10), 112.6 (C1/2), 55.4 (NCH$_2$), 23.2 (CH$_2$), 10.8 (CH$_3$), C5/8 is not detected.

Elemental analysis: C$_{14}$H$_{18}$I$_2$N$_4$Pd calculated: C, 27.91; H, 3.01; N, 9.30.

found: C, 27.50; H, 2.75; N, 8.83.

Example 38: Rh Carbene Complex

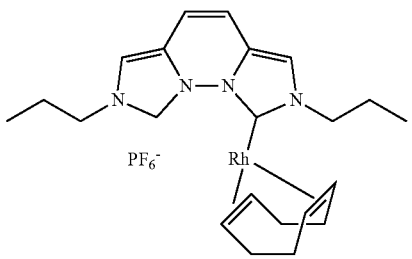

Bisimidazolium salt, Ex. 16 (10.0 mg, 18.7 μmol), [Rh(μ-Cl)(cod)]$_2$ (4.6 mg, 9.3 μmol) and KOAc (1.8 mg, 19 μmol) are suspended in CD$_3$CN (0.5 ml). A yellow suspension with a pale solid forms, which, after 3 h, exhibits complete conversion and formation of the asymmetrical Rh(I) complex.

$^1$H-NMR (CD$_3$CN, 400.13 MHz):

δ=12.63 (s, br, 1H, 8-H), 7.83 (d, 1H, $^4J_{HH}$=1.8 Hz, 10-H), 7.67 (s, 1H, 3-H), 7.25 (d, 1H, $^3J_{HH}$=10.3 Hz, 1-H), 7.12 (d, 1H, $^3J_{HH}$=10.3 Hz, 2-H), 5.18-5.28 (m, 2H, =CH$_{cod}$), 4.96 (ddd, $^2J_{HH}$=13.2 Hz, $^3J_{HH}$=8.8 Hz, $^3J_{HH}$=6.3 Hz, 1H, 11-H), 4.59 (ddd, $^2J_{HH}$=13.2 Hz, $^3J_{HH}$=8.7 Hz, $^3J_{HH}$=6.4 Hz, 1H, 11-H), 4.45-4.58 (m, 2H, 11'-H), 3.61-3.69 (m, 1H, =CH$_{cod}$), 3.49-3.57 (m, 1H, =CH$_{cod}$), 2.37-2.60 (m, 4H, CH$_{2cod}$), 2.02-2.23 (m, 8H, CH$_{2cod}$, 12/12'-H), 1.08 (t, 3H, $^3J_{HH}$=7.4 Hz, 13-H), 1.05 (t, 3H, $^3J_{HH}$=7.4 Hz, 13'-H).

$^{13}$C{$^1$H}-NMR (CD$_3$CN, 100.61 MHz):

δ=127.2 (C10a), 127.1 (C2a), 126.0 (C8), 119.0 (C3), 117.9 (C10), 117.3 (C1), 111.9 (C2), 102.5 (d, $^1J_{RhC}$=7.1 Hz, =CH$_{cod}$), 101.4 (d, $^1J_{RhC}$=7.1 Hz, =CH$_{cod}$), 74.1 (br, =CH$_{cod}$), 56.2 (C11), 54.2 (C11'), 34.1 (CH$_{2cod}$), 32.4 (CH$_{2cod}$), 30.0 (CH$_{2cod}$), 29.4 (CH$_{2cod}$), 25.2 (C12), 24.5 (C12'), 11.5 (C13), 10.9 (C13').

Example 39: Rh Carbene Complex

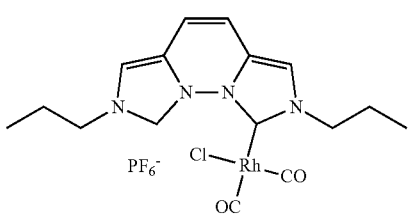

Bisimidazolium salt, Ex. 16 (15.0 mg, 28.1 μmol), [Rh(μ-Cl)(CO)]$_2$ (5.5 mg, 14 μmol) and KOAc (2.8 mg, 28 μmol) are suspended in CD$_3$CN (0.5 ml). A yellow suspension with a pale solid forms, which, after 3 h at 40° C., exhibits complete conversion and formation of the asymmetrical Rh(I) complex.

$^1$H-NMR (CD$_3$CN, 400.13 MHz):

δ=11.46 (d, 1H, $^4J_{HH}$=1.6 Hz, 8-H), 7.85 (d, 1H, $^4J_{HH}$=1.6 Hz, 10-H), 7.36 (d, 1H, $^3J_{HH}$=10.3 Hz, 1-H), 7.23 (d, 1H, $^3J_{HH}$=10.3 Hz, 2-H), 4.50-4.62 (m, 2H, 11-H), 4.45 (t, 2H, $^3J_{HH}$=7.1 Hz, 11'-H), 1.97-2.09 (m, 4H, 12/12'-H), 1.00 (t, 3H, $^3J_{HH}$=7.4 Hz, 13-H), 0.99 (t, 3H, $^3J_{HH}$=7.4 Hz, 13'-H).

$^{13}$C{$^1$H}-NMR (CD$_3$CN, 100.61 MHz):

δ=186.0 (d, $^1J_{RhC}$=56.0 Hz, CO), 182.2 (d, $^1J_{RhC}$=73.0 Hz, CO), 165.6 (d, $^1J_{RhC}$=44.7 Hz, C5), 127.6 (C2a), 127.0 (C10a), 126.4 (C8), 119.6 (C3), 117.9 (C10), 117.0 (C1), 112.9 (C2), 56.7 (C11), 53.9 (C11'), 25.1 (C12), 24.6 (C12'), 11.2 (C13), 10.7 (C13').

Example 40: Rh Carbene Complex

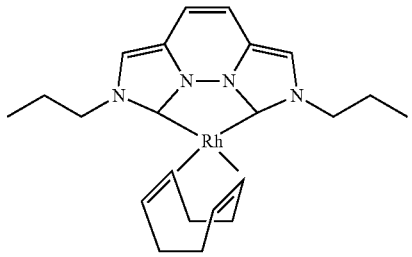

Deprotonation Using KOAc:

KOAc (1.8 mg, 19 μmol) is added to a solution of asymmetrical Rh(I) complex, Ex. 38, generated in situ (11.9 mg, 18.7 μmol) in 0.5 ml of abs. CD$_3$CN. During this addition, the solution becomes somewhat darker, and, after 30 min, conversion to the symmetrical complex can be observed by NMR spectroscopy.

Deprotonation Using Ag$_2$O:

Ag$_2$O (3.3 mg, 14 μmol) is added to a solution of asymmetrical Rh(I) complex, Ex. 38, generated in situ (16.8 mg, 28.1 mol) in 0.5 ml of abs. CD$_3$CN. A grey solid precipitates out, and the formation of the symmetrical complex can be followed by NMR spectroscopy.

$^1$H-NMR (CD$_3$CN, 400.13 MHz):

δ=7.44 (s, 2H, 3/10-H), 7.16 (s, 2H, 1/2-H), 5.37 (s, br, 4H, CH$_{cod}$), 3.96 (t, 4H, $^3J_{HH}$=7.4 Hz, NCH$_2$), 2.33-2.36 (m, 4H, CH$_{2cod}$), 2.18-2.24 (m, 4H, CH$_{2cod}$), 1.90 (sext, 4H, $^3J_{HH}$=7.4 Hz, CH$_2$), 0.96 (t, 6H, $^3J_{HH}$=7.4 Hz).

$^{13}$C{$^1$H}-NMR (CD$_3$CN, 100.61 MHz):

δ=160.9 (d, $^1J_{RhC}$=54.2 Hz, C5/8), 122.5 (C2a/10a), 117.7 (C3/10), 114.8 (C1/2), 86.8 (d, $^1J_{RhC}$=9.0 Hz, CH$_{cod}$), 52.8 (NCH$_2$), 31.7 (CH$_{2cod}$), 31.5 (CH$_{2cod}$), 26.0 (CH$_2$), 11.2 (CH$_3$).

Example: Production of OLEDs

OLEDs according to the invention are produced by a general process in accordance with WO 2004/058911, which is adapted to the circumstances described here (layer-thickness variation, materials used).

The results for various OLEDs are presented in Examples 41 to 49 below (Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have in principle the following layer structure: substrate/hole-injection layer (HIL)/hole-transport layer (HTL)/emission layer (EML)/hole-blocking layer (HBL)/electron-transport layer (ETL)/electron-injection layer (EIL) and finally a cathode. The cathode is formed by an aluminium layer with a thickness of 100 nm Firstly, vacuum-processed OLEDs are described. For this purpose, all materials are applied by thermal vapour deposition in a vacuum chamber. The emission layer here always consists of at least one matrix material (host material) and an emitting dopant (emitter), with which the matrix material or matrix materials is (are) admixed in a certain proportion by volume by co-evaporation. An expression such as M1:M2:Ex. XY (55%:35%:10%) here means that material M1 is present in the layer in a proportion by volume of 55%, M2 is present in the layer in a proportion of 35% and the emitter according to Ex. XY is present in the layer in a proportion of 10%. The precise structure of the OLEDs is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a particular initial luminous density. The expression LT50 means that the lifetime given is the time at which the luminous density has dropped to 50% of the initial luminous density, i.e. from, for example, 4000 cd/m$^2$ to 2000 cd/m$^2$. Different initial luminances are selected depending on the emission colour. The values for the lifetime can be converted into a figure for other initial luminous densities with the aid of conversion formulae known to the person skilled in the art. The lifetime for an initial luminous density of 1000 cd/m$^2$ is the usual figure here.

Use of Compounds According to the Invention as Emitter Materials in Phosphorescent OLEDs The compounds according to the invention can be employed, inter alia, as phosphorescent emitter materials in the emission layer in OLEDs. The metal complexes containing the central atoms Ir and Pt are used here. The results for the OLEDs are summarised in Table 2. In the case of the OLEDs, it is found here that the materials according to the invention result in efficient emitting OLEDs.

TABLE 1

Structure of the OLEDs

| Ex. | HTL1 Thickness | HTL2 Thickness | HTL3 Thickness | EML Thickness | HBL Thickness | ETL Thickness | EIL Thickness |
|---|---|---|---|---|---|---|---|
| 41 | HIM 70 nm | HTM 1 5 nm | HTM 2 90 nm | M1:24 (90%:10%) 40 nm | M1 10 nm | ETM1 30 nm | LiQ 2 nm |

TABLE 1-continued

Structure of the OLEDs

| Ex. | HTL1 Thickness | HTL2 Thickness | HTL3 Thickness | EML Thickness | HBL Thickness | ETL Thickness | EIL Thickness |
|---|---|---|---|---|---|---|---|
| 42 | HIM 70 nm | HTM 1 5 nm | HTM 2 90 nm | M1:25 (85%:15%) 40 nm | M1 10 nm | ETM1 30 nm | LiQ 2 nm |
| 43 | HIM 70 nm | HTM 1 5 nm | HTM 2 90 nm | M1:26 (95%:5%) 40 nm | M1 10 nm | ETM1 30 nm | LiQ 2 nm |
| 44 | HIM 70 nm | HTM 1 5 nm | HTM 2 90 nm | M1:27 (90%:10%) 40 nm | M1 10 nm | ETM1 30 nm | LiQ 2 nm |
| 45 | HIM 70 nm | HTM 1 5 nm | HTM 2 90 nm | M1:28 (90%:10%) 40 nm | M1 10 nm | ETM1 30 nm | LiQ 2 nm |
| 46 | HIM 70 nm | HTM 1 5 nm | HTM 2 90 nm | M1:M2:29 (60%:30%:10%) 40 nm | M1 10 nm | ETM1 30 nm | LiQ 2 nm |
| 47 | HIM 70 nm | HTM 1 5 nm | HTM 2 90 nm | M1:M2:29 (70%:20%:10%) 40 nm | M1 10 nm | ETM1 30 nm | LiQ 2 nm |
| 48 | HIM 70 nm | HTM 1 5 nm | HTM 2 90 nm | M1:M2:29 (70%:25%:5%) 40 nm | M1 10 nm | ETM1 30 nm | LiQ 2 nm |
| 49 | HIM 70 nm | HTM 1 5 nm | HTM 2 90 nm | M1:M2:29 (70%:20%:10%) 40 nm | M1 10 nm | ETM1 30 nm | LiQ 2 nm |

TABLE 2

Use of compounds according to the invention as emitters in phosphorescent OLEDs

| Ex. | EQE (%) at 1000 cd/m² | Voltage (V) at 1000 cd/m² | CIE x/y at 1000 cd/m² | LT50 (h) At 1000 cd/m² |
|---|---|---|---|---|
| 41 | 6.9 | 6.9 | 0.32/0.65 | 850 |
| 42 | 5.9 | 6.8 | 0.32/0.64 | — |
| 43 | 9.2 | 7.4 | 0.31/0.66 | — |
| 44 | 8.3 | 7.2 | 0.32/0.65 | — |
| 45 | 7.0 | 7.0 | 0.33/0.63 | 1200 |
| 46 | 12.4 | 4.4 | 0.51/0.47 | 17000 |
| 47 | 10.2 | 5.2 | 0.33/0.63 | — |
| 48 | 8.9 | 4.8 | 0.32/0.66 | 900 |
| 49 | 9.5 | 4.9 | 0.33/0.63 | 350 |

TABLE 3

Structural formulae of the materials used

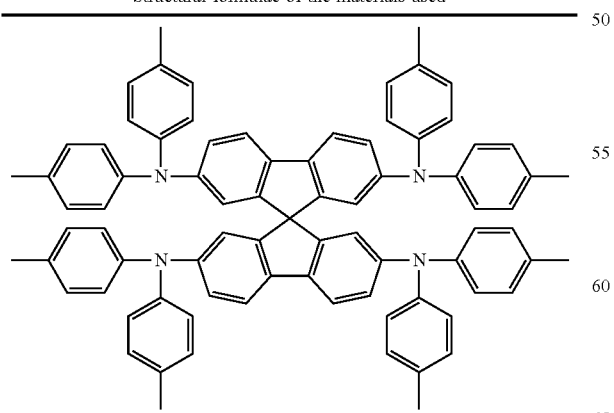

HIM

TABLE 3-continued

Structural formulae of the materials used

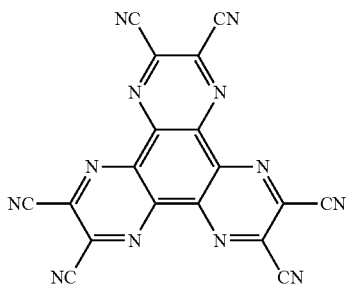 [SMILES: N#Cc1nc2c3nc(C#N)c(C#N)nc3c3nc(C#N)c(C#N)nc3c2nc1C#N]

HTM 1

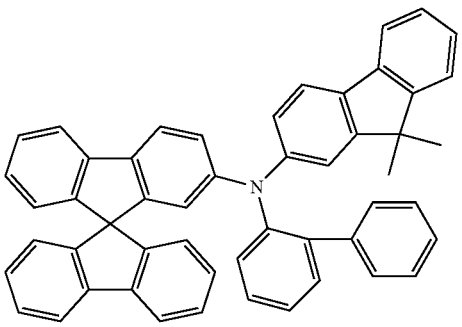 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HTM 2

TABLE 3-continued

Structural formulae of the materials used

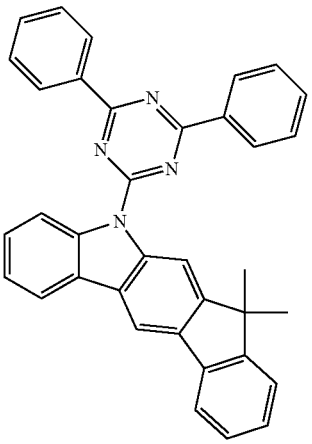 [SMILES: CC1(C)c2ccccc2-c2cc3c4ccccc4n(-c4nc(-c5ccccc5)nc(-c5ccccc5)n4)c3cc21]

M1

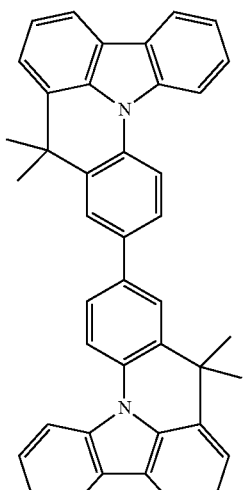

M2

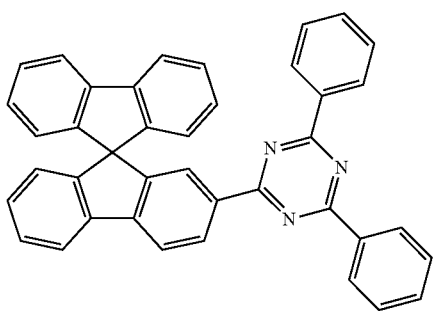 [SMILES: c1ccc(-c2nc(-c3ccccc3)nc(-c3ccc4c(c3)C3(c5ccccc5-c5ccccc53)c3ccccc3-4)n2)cc1]

ETM

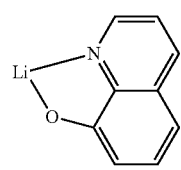

LiQ

Materials according to the invention can also be used from solution, where they result in simpler OLEDs compared with vacuum-processed OLEDs having nevertheless good properties. The production of components of this type is based on the production of polymeric light-emitting diodes (PLEDs), which has already been described many times in the literature (for example in WO 2004/037887). The structure is composed of substrate/ITO/PEDOT (80 nm)/interlayer/emission layer (80 nm)/cathode. The interlayer used serves for hole injection; in this case, HIL-012 from Merck is used. In the present case, the emitters according to the invention are dissolved in toluene or THF for the emission layer besides the matrix. The typical solids content of such solutions is between 16 and 25 g/l if, as here, the typical layer thickness of 80 nm for a device is to be achieved by means of spin coating. The emission layer is applied by spin-coating in an inert-gas atmosphere, in the present case argon, and dried by heating at 120° C. for 10 min. Finally, a cathode comprising barium and aluminium is applied by vacuum vapour deposition. The layers HBL and ETL used in the above-mentioned examples can also be applied between EML and cathode by vapour deposition, the interlayer may also be replaced by one or more layers, which merely have to satisfy the condition of not being detached again by the subsequent processing step of EML deposition from solution. The solution-processed devices are characterised as standard in the matrices PS (polystyrene):M1:M2: Ex. XY (30%:20%:40%:10%), the said OLED examples have not yet been optimised. Table 4 summarises the data obtained. In the case of the solution-processed OLEDs, it is found here that the materials according to the invention result in efficient emitting OLEDs.

TABLE 4

Results with solution-processed materials

| Ex. | EQE (%) at 1000 cd/m² | Voltage (V) at 1000 cd/m² | CIE x/y at 1000 cd/m² |
| --- | --- | --- | --- |
| 50 | 8.9 | 8.8 | 0.42/0.55 |
| 51 | 5.8 | 9.0 | 0.38/0.47 |
| 52 | 4.1 | 8.1 | 0.41/0.49 |

The invention claimed is:

1. A compound of the formula (1a), (2a) or (3a),

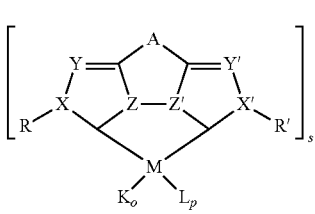

formula (1a)

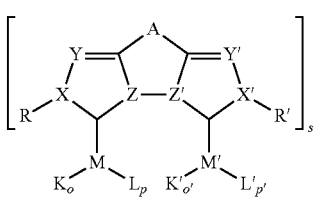

formula (2a)

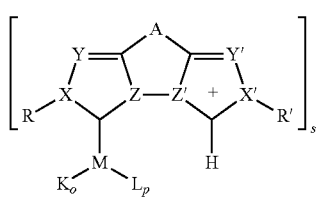

formula (3a)

where the symbols and indices used have the following meanings:

M, M' is on each occurrence, identically or differently, from the group consisting of Fe, Ru, Os, Co, Rh, Ir, Ni, Pd, Pt, Cu, Ag, Au, Ti, Zr, V, Mn, Sc, Cr, Mo and W;

R, R' is, identically or differently independently of one another, hydrogen, straight-chain or branched alkyl having 1-20 C atoms, straight: chain or branched alkenyl having 2-20 C atoms and at least one double bond, straight-chain or branched alkynyl having 2-20 C atoms and at least one triple bond, saturated, partially or fully unsaturated cycloalkyl having 3-10 C atoms, which may be substituted by alkyl groups having 1-10 C atoms, unsubstituted or substituted aryl or aromatic ring system, unsubstituted or substituted heterocycle or heteroaromatic ring system or substituted or unsubstituted aralkyl or heteroaralkyl, where one or both substituents R and R' may be partially substituted in any desired position or fully substituted by halogen or partially substituted in any desired position by CN or $NO_2$, and halogen is selected from F, Cl, Br and I, and where a carbon atom of one or both substituents R and R' may be replaced by atoms and/or atom groups selected from the group —O—, —C(O)—, —C(O)O—, —S—, —S(O)—, —$SO_2$—, —$SO_3$—, —N═, —N═N—, —NH—, —$NR^1$—, —$PR^1$—, —P(O)$R^1$—, —P(O)$R^1$—O—, —O—P(O)$R^1$—O—, and —P($R^1$)$_2$═N—, where $R^1$ is unfluorinated, partially or perfluorinated alkyl having 1-6 C atoms, saturated or partially unsaturated cycloalkyl having 3-10 C atoms, unsubstituted or substituted aryl or saturated or unsaturated, unsubstituted or substituted heterocycle;

X, X' is, identically or differently independently of one another, C, $CR^2$ or N and where $R^2$ has, identically or differently, the same meaning as R or R', and where $R^2$ may be linked to R or R' to form a 3- to 20-membered ring, and where no radical R or R' is bonded to X or X' if X or X' stands for O or S;

A is —$CR^4$═$CR^4$—, —$CR^4$═N— or —$CR^4R^5$—$CR^4R^5$— and wherein $R^4$ and $R^5$ may be identical or different and have, independently of one another, the same meaning as R or R' or are a halogen F, Cl, Br, I, where, in the case of carbon, the unit may optionally be interrupted one or more times at any desired position by heteroatoms N, P, O, S;

Y, Y' is, identically or differently independently of one another, $CR^6$ or N and $R^6$ has the same meaning as R or R', or is a bridging unit consisting of one to three bridge atoms;

Z, Z' is, identically or differently independently of one another, $CR^8$ or N;

with the proviso that at least one atom from X, Y, Z and at least one atom from X', Y' and Z' contains, identically or independently of one another, a N atom where $R^8$ has, identically or differently, the same meaning as R or R', and where the radicals $R^8$ of Z and Z' may be linked to one another with formation of a ring;

K, K' is on each occurrence, identically or differently, a mono-, di- or trianionic ligand, which may be mono-, bi, tri-, tetra-, penta- or hexadentate;

L, L' is on each occurrence, identically or differently, a neutral mono-, bi, tri-, tetra-, penta- or hexadentate ligand;

o, o' is on each occurrence, identically or differently, the number of ligands K or K' from 0 to 6, where the ligands K and K' may be identical or different in the case of o greater than 1;

p, p' is on each occurrence, identically or differently, the number of ligands L or L' from 0 to 6, where the ligands L and L' may be identical or different in the case of p greater than 1;

where o or o' is selected so that the charge of all ligands K and K' corresponds to the valence of the metal atom employed, and the sum of o and p or o' and p' is dependent on the coordination number of the metal atom employed and the index s and the denticity of the ligand K and L or K' and L', where K or K' may also be weakly coordinating or non-coordinating and, as counterion, balances the charge of the metal complex, where s is an integer from 1 to 3, so that the metal complex contains 1, 2 or 3 biscarbene ligands, which may be identical or different independently of one another, where, depending on the metal atom M and M', ligand $L_p$, $L'_p$, $K_o$, $K'_{o'}$ and steric influences of the biscarbene ligand may also form a very weak or only a coordinative bond to the metal atom, where, in addition, two or more radicals which are bonded to the same atom or to adjacent atoms may form an aromatic, heteroaromatic or aliphatic ring system with one another, and where, in addition, two or more ligands may be connected to one another via a group R or R' and thus may form a tetradentate ligand system or a polypodal ligand or the groups R and/or R' may coordinate to M or M'.

2. The compound according to claim 1, wherein M and M' are selected, identically or differently on each occurrence, from the group consisting of Fe, Ru, Os, Co, Rh, Ir, Ni, Pd, Pt, Cu, Ag, Au, Ti, Zr, V, Mn, Sc, Cr, Mo and W.

3. The compound according to claim 1, wherein R and R' are selected, identically or differently on each occurrence, from the group consisting of straight-chain or branched alkyl having 1-10 C atoms, saturated cycloalkyl having 3-6 C atoms, which may be substituted by alkyl groups having 1-4 C atoms, unsubstituted or substituted aryl or aromatic ring system, unsubstituted or substituted heterocycle or heteroaromatic ring system or substituted or unsubstituted aralkyl or heteroaralkyl, and where a carbon atom of one or both substituents R and R' may be replaced by —O—; or in that R or R', if this is coordinated to the metal, stands for a substituted or unsubstituted aralkyl or heteroaralkyl group, in which, in addition, a C atom may be replaced by O, S or NR.

4. The compound according to claim 1, selected from the compounds of the formulae (1b), (2b) and (3b), formula (1b)

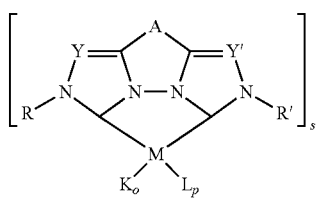

formula (2b)

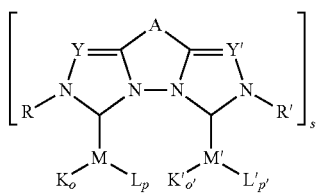

formula (3b)

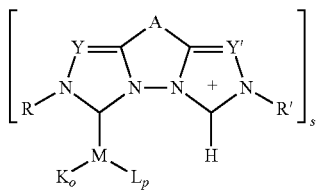

where R, R', $R^1$ to $R^8$, K, K', L, L', o, o', p, p' and s have the meanings given in claim 1 and the other symbols and indices used have the following meanings:

M, M' is selected on each occurrence, identically or differently, from the group consisting of Ir, Pt and Cu;

A is —$CR^4$=$CR^4$— or —$CR^4$=N; and

Y, Y' is, identically or differently independently of one another, $CR^6$ or N.

5. The compound according to claim 1, selected from the compounds of the formulae (1c), (1d), (2c), (2d) and (3c), formula (1c)

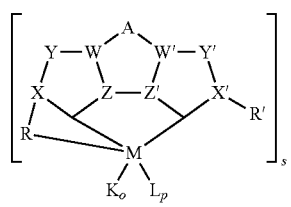

formula (1d)

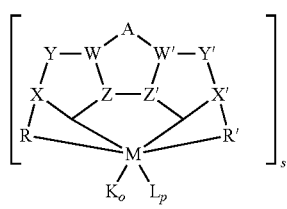

formula (2c)

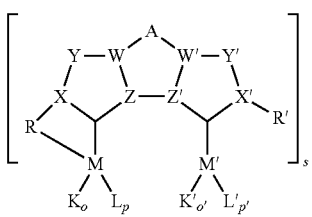

formula (2d)

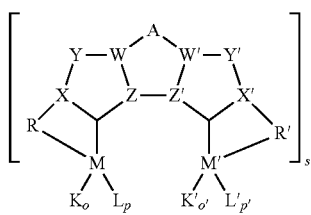

formula (3c)

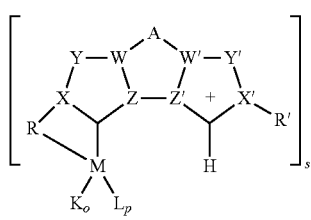

where the symbols and indices used have the meanings given in claim 1 and W, W' is C.

6. The compound according to claim 1, wherein the ligands K and K' are selected from the group consisting of hydride, deuteride, F, Cl, Br, I, pseudohalides, azide, trifluorosulfonates, alkylacetylides, aryl- or heteroarylacetylides, alkyl groups, alkylaryl radicals, aryl groups, which may also be bidentate or polydentate, heteroaryl groups, which may also be bidentate or polydentate, hydroxide, cyanide, cyanate, isocyanate, thiocyanate, isothiocyanate, aliphatic or aromatic alcoholates, aliphatic or aromatic thioalcoholates, amides, carboxylates, anionic, nitrogen-containing heterocycles, aliphatic and aromatic phosphides $PR_2^-$, aliphatic or aromatic selenides $SeR^-$, cyclopentadienyl (Cp), where the cyclopentadienyl groups may be substituted by alkyl substituents, indenyl, where the indenyl radical may be substituted by alkyl substituents, $O^{2-}$, $S^{2-}$, nitrenes, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, and dithiolates derived from dithiols.

7. The compound according to claim 1, wherein L and L' are selected from the group consisting of amines, ethers, water, alcohols, carbon monoxide, nitriles, nitrogen monoxide, isonitriles, olefins, nitrogen-containing heterocycles, phosphines, phosphonates, arsenates, phosphites, arsines, stibines, aliphatic or aromatic sulfides, aliphatic or aromatic selenides, carbenes, acetylenically unsaturated multiple-bond systems, diamines, imines, heterocycles containing two nitrogen atoms, diphosphines and conjugated dienes.

8. A formulation comprising at least one compound according to claim 1 and at least one solvent.

9. A compound of the formula (4) or formula (5), formula (4)

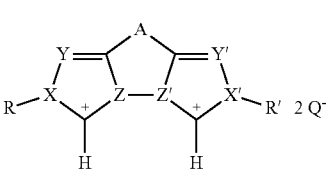

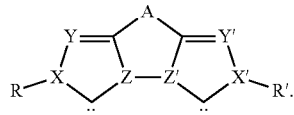

formula (5)

where
R, R' is, identically or differently independently of one another, hydrogen, straight-chain or branched alkyl having 1-20 C atoms, straight-chain or branched alkenyl having 2-20 C atoms and at least one double bond, straight-chain or branched alkynyl having 2-20 C atoms and at least one triple bond, saturated, partially or fully unsaturated cycloalkyl having 3-10 C atoms, which may be substituted by alkyl groups having 1-10 C atoms, unsubstituted or substituted aryl or aromatic ring system, unsubstituted or substituted heterocycle or heteroaromatic ring system or substituted or unsubstituted aralkyl or heteroaralkyl, where one or both substituents R and R' may be partially substituted in any desired position or fully substituted by halogen or partially substituted in any desired position by CN or $NO_2$, and halogen is selected from F, Cl, Br and I, and where a carbon atom of one or both substituents R and R' may be replaced by atoms and/or atom groups selected from the group —O—, —C(O)—, —C(O)O—, —S—, —S(O)—, —$SO_2$—, —$SO_3$—, —N═, —N═N—, —NH—, —$NR^1$—, —$PR^1$—, —P(O)$R^1$—, —P(O)$R^1$—O—, —O—P(O)$R^1$—O—, and —P($R^1$)$_2$═N—, where $R^1$ is unfluorinated, partially or perfluorinated alkyl having 1-6 C atoms, saturated or partially unsaturated cycloalkyl having 3-10 C atoms, unsubstituted or substituted aryl or saturated or unsaturated, unsubstituted or substituted heterocycle;
X, X' is, identically or differently independently of one another, C, $CR^2$ or N and where $R^2$ has, identically or differently, the same meaning as R or R', and where $R^2$ may be linked to R or R to form a 3- to 20-membered ring;
A is —$CR^4$═$CR^4$—, —$CR^4$═N— or —$CR^4R^5$—$CR^4R^5$— and wherein $R^4$ and $R^5$ may be identical or different and have, independently of one another, the same meaning as R or R' or are a halogen F, Cl, Br, I, where, in the case of carbon, the unit may optionally be interrupted one or more times at any position by heteroatoms N, P, O, S;
Y, Y' is, identically or differently independently of one another, $CR^6$ or N and $R^6$ has the same meaning as R or R', or is a bridging unit consisting of one to three bridge atoms;
Z, Z' is, identically or differently independently of one another, $CR^8$ or N;
with the proviso that at least one atom from X, Y, Z and at least one atom from X', Y', Z' contains, identically or independently of one another, a N atom where $R^8$ has, identically or differently, the same meaning as R or R', and where the radicals $R^8$ of Z and Z' may be linked to one another with formation of a ring;
and Q⁻ is an anionic counterion and where the compound of the formula (5) may also be in partially protonated form, resulting in a monocarbene.

10. A process for the preparation of the compound according to claim 1 by reaction of a compound of the formula (4) or formula (5),

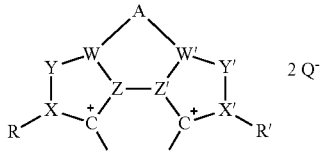

formula (4)

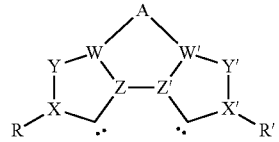

formula (5)

where R, R', X, X', A, Y, Y', Z, Y' have the meanings given in claim 1 and

W, W' is C and Q⁻ is an anionic counterion and where the compound of the formula (5) may also be in partially protonated form, resulting in a monocarbine, as bis- or monocarbene ligand by deprotonation of ligand precursors or by complexing of mono- or biscarbene ligands or by oxidative addition of haloformamidinium derivatives or by the cleavage of electron-rich olefins by means of metal compounds or by the transmetallation of metal carbene complexes.

11. An organocatalyst or an ionic liquid which comprises the compound according to claim 9.

12. A process which comprises utilizing the compound according to claim 1 wherein the process is selected from the group consisting of carbonylation, hydroamination, hydrogenation, hydroaminomethylation, hydroformylation, hydrosilylation, hydrocyanation, hydrodimerisation, oxidation, oxidative coupling, Heck reaction, Tsuji-Trost coupling, Suzuki-Miyaura coupling, Kumada coupling, Negishi coupling, Stille coupling, Sonogashira reaction, C(sp3)-C(sp3) coupling reactions, C(sp3)-C(sp2) coupling reactions, Hartwig- Buchwald amination, Ullmann-Goldberg coupling, isomerisation, rearrangement, Diels-Alder reaction, metathesis, C—H activation of alkanes and alkenes, 1,4-functionalisation of 1,3-diener, telomerisation, oligomerisation and polymerization.

13. An electronic device comprising at least one compound according to claim 1.

14. An organic electro luminescent device comprising the compound according to claim 1 is employed as emitting compound in one or more emitting layers.

15. The electronic device according to claim 13, wherein the device is an organic electroluminescent device, organic integrated circuit, organic field-effect transistor, organic thin-film transistor, organic light-emitting transistor, organic solar cell, organic optical detector, organic photoreceptor, organic field-quench device, light-emitting electrochemical cell or organic laser diode.

16. The compound according to claim 1, wherein M and M' are selected, identically or differently on each occurrence, from the group consisting of Ir, Pt and Cu.

17. The compound according to claim 4, wherein
A is —$CR^4$═$CR^4$—.

18. The formulation as claimed in claim 8, wherein the formulation is a solution, a suspension or a mini-emulsion.

* * * * *